United States Patent
Fyfe et al.

(10) Patent No.: US 7,262,196 B2
(45) Date of Patent: Aug. 28, 2007

(54) TRI(CYCLO) SUBSTITUTED AMIDE GLUCOKINASE ACTIVATOR COMPOUNDS

(75) Inventors: Matthew Colin Thor Fyfe, Oxford (GB); Lisa Sarah Gardner, Oxford (GB); Maseo Nawano, Toda (JP); Martin James Procter, Oxford (GB); Chrystelle Marie Rasamison, Oxford (GB); Geoffrey Martyn Williams, Oxford (GB); David Witter, Putnam Valley, NY (US); Arlindo Castelhano, New City, NY (US); Kosuke Yasuda, Toda (JP)

(73) Assignee: Prosidion Limited, Oxford (GB)

( * ) Notice: Subject to any disclaimer, the term of this patent is extended or adjusted under 35 U.S.C. 154(b) by 487 days.

(21) Appl. No.: 10/776,559

(22) Filed: Feb. 10, 2004

(65) Prior Publication Data
US 2004/0186290 A1 Sep. 23, 2004

Related U.S. Application Data

(60) Provisional application No. 60/512,826, filed on Oct. 20, 2003, provisional application No. 60/446,682, filed on Feb. 11, 2003.

(51) Int. Cl.
*A61K 31/498* (2006.01)
*A61K 31/506* (2006.01)
*C07D 43/14* (2006.01)

(52) U.S. Cl. .................. 514/252.1; 514/256; 544/238; 544/333; 544/405; 546/256

(58) Field of Classification Search ................ 544/238, 544/405; 546/256
See application file for complete search history.

(56) References Cited

U.S. PATENT DOCUMENTS 6,911,545 B2 * 6/2005 Corbett et al. ............ 546/270.7
7,132,425 B2 * 11/2006 Chen et al. ............ 514/255.05

* cited by examiner

*Primary Examiner*—Kamal A. Saeed
(74) *Attorney, Agent, or Firm*—Shu M. Lee; James Myers

(57) ABSTRACT

Compounds of Formula (I):

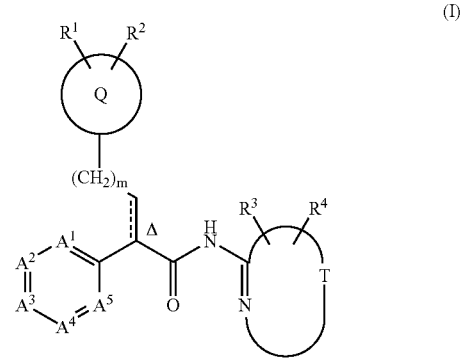

or pharmaceutically acceptable salts or N-oxides thereof, are useful in the prophylactic and therapeutic treatment of hyperglycemia and diabetes.

17 Claims, No Drawings

TRI(CYCLO) SUBSTITUTED AMIDE GLUCOKINASE ACTIVATOR COMPOUNDS

This application claims the benefit of U.S. Provisional Application Ser. No. 60/446,682 filed Feb. 11, 2003 and U.S. Provisional Application Ser. No. 60/512,826 filed Oct. 20, 2003.

BACKGROUND OF THE INVENTION

The present invention is directed to tri(cyclo) substituted amide compounds. In particular, the present invention is directed to amide compounds substituted i) at the carbonyl carbon with an ethyl/ethenyl attached to a nitrogen-containing six-membered heteroaryl ring and a saturated or unsaturated ring, and ii) at the amino with a nitrogen bearing heteroaryl ring, which are modulators of glucokinase and are useful in the prophylactic or therapeutic treatment of hyperglycemia and type II diabetes.

Glucokinase ("GK") is believed to be important in the body's regulation of its plasma glucose level. GK, found principally in the liver and pancreas, is one of four hexokinases that catalyze the initial metabolism of glucose. The GK pathway is saturated at higher glucose levels than the other hexokinase pathways (See R. L. Printz et al., *Annu. Rev. Nutr.*, 13:463-496(1993)). GK is critical to maintaining the glucose balance in mammals. Animals that do not express GK die soon after birth with diabetes, while animals that overexpress GK have improved glucose tolerance. Activation of GK can lead to hyperinsulinemic hypoglycemia. (See, for example, H. B. T. Christesen et al., *Diabetes*, 51:1240-1246(2002)). Additionally, type II maturity-onset diabetes of the young is caused by the loss of function mutations in the GK gene, suggesting that GK operates as a glucose sensor in humans. (Y. Liang et al., *Biochem. J.* 309:167-173(1995)). Thus, compounds that activate GK increase the sensitivity of the GK sensory system and would be useful in the treatment of hyperglycemia—particularly the hyperglycemia associated with type II diabetes. It is therefore desirable to provide novel compounds that activate GK to treat diabetes.

International Patent Publication No. WO2001044216 and U.S. Pat. No. 6,353,111 describe (E)-2,3-disubstituted-N-heteroarylacrylamides as GK activators. International Patent Publication No. WO2002014312 and U.S. Pat. Nos. 6,369,232, 6,388,088, and 6,441,180 describe tetrazolylphenylacetamide GK activators. International Patent Publication No. WO2000058293, European Patent Application No. EP 1169312 and U.S. Pat. No. 6,320,050 describe arylcycloalkylpropionamide GK activators. International Patent Publication No. 2002008209 and U.S. Pat. No. 6,486,184 describe alpha-acyl and alpha-heteroatom-substituted benzene acetamide GK activators as anti-diabetic agents. International Patent Publication No. WO2001083478 describes hydantoin-containing GK activators. International Patent Publication No. WO2001083465 and U.S. Pat. No. 6,388,071 describe alkynylphenyl heteroaromatic GK activators. International Patent Publication No. WO2001085707 and U.S. Pat. No. 6,489,485 describe para-amine substituted phenylamide GK activators. International Patent Publication No. WO2002046173 and U.S. Pat. Nos. 6,433,188, 6,441,184, and 6,448,399 describe fused heteroaromatic GK activators. International Patent Publication No. WO2002048106 and U.S. Pat. No. 6,482,951 describe isoindolin-1-one GK activators. International Patent Publication No. WO2001085706 describes substituted phenylacetamide GK activators for treating type II diabetes. U.S. Pat. No. 6,384,220 describes para-aryl or heteroaryl substituted phenyl GK activators. French Patent No. 2,834,295 describes methods for the purification and crystal structure of human GK and discloses 3-cyclopentyl-2-pyridin-4-yl-N-thiazol-2-ylpropionamide as a GK ligand. International Patent Publication No. WO2003095438, published after the priority date of the present application, describes N-heteroaryl phenylacetamides and related compounds as GK activators for the treatment of type II diabetes. U.S. Pat. No. 6,610,846 describes the preparation of cycloalkylheteroaryl propionamides as GK activators. International Patent Publication No. WO2003000262 describes vinyl phenyl GK activators. International Patent Publication No. WO2003000267 describes aminonicotinate derivatives as GK modulators. International Patent Publication No. WO2003015774, published after the priority date of the present application, describes compounds as GK modulators. International Patent Publication No. WO2003047626, published after the priority date of the present application, describes the use of a GK activator in combination with a glucagon antagonist for treating type II diabetes. International Patent Publication No. WO2003055482, published after the priority date of the present application, describes amide derivatives as GK activators. International Patent Publication No. WO2003080585, published after the priority date of the present application, describes aminobenzamide derivatives with GK activity for the treatment of diabetes and obesity. International Patent Publication No. WO2003097824, published after the priority date of the present application, describes human liver GK crystals and their used for structure-based drug design. International Patent Publication No. WO2004002481, published after the priority date of the present application, discloses arylcarbonyl derivatives as GK activators.

SUMMARY OF THE INVENTION

Compounds represented by Formula (I):

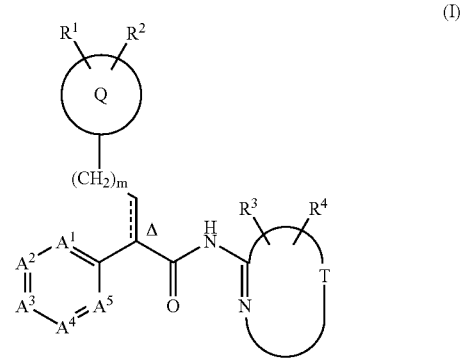

or pharmaceutically acceptable salts or N-oxides thereof, are useful in the prophylactic or therapeutic treatment of hyperglycemia and type II diabetes.

DETAILED DESCRIPTION OF THE INVENTION

The present invention is directed to a compound of Formula (I):

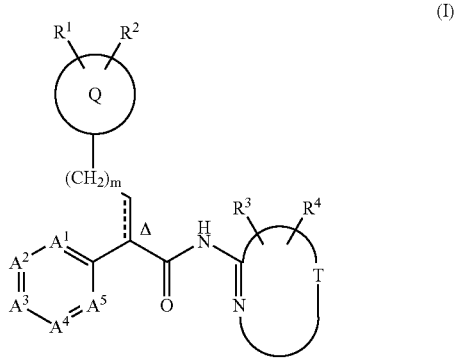

(I)

or a pharmaceutically acceptable salt or N-oxide thereof, wherein:

one of $A^1$, $A^2$, $A^3$, $A^4$ and $A^5$ is N, another of them is C—$R^5$, another of them is C—$R^6$, and the other two are independently either N or CH;

Q is a $C_{3-8}$cycloalkyl, a 5- or 6-membered heteroaryl, or a 4-8-membered heterocyclic ring;

T together with the —N=C— to which it is attached forms a heteroaryl ring, or a heterocyclic ring where the N=C bond is the only site of unsaturation;

$R^1$ and $R^2$ each independently are hydrogen, halogen, hydroxy, cyano, nitro, vinyl, ethynyl, methoxy, $OCF_nH_{3-n}$, —$N(C_{0-4}alkyl)(C_{0-4}alkyl)$, CHO, or $C_{1-2}$alkyl optionally substituted with 1-5 independent halogen, hydroxy, cyano, methoxy, —$N(C_{0-2}alkyl)(C_{0-2}alkyl)$, $SOCH_3$, or $SO_2CH_3$ substituents; or $R^1$ and $R^2$ together form a carbocyclic or heterocyclic ring; or $R^1$ and $R^2$ may be taken together to represent an oxygen atom attached to the ring via a double bond;

$R^3$ and $R^4$ each independently are hydrogen, halogen, $OCF_nH_{3-n}$, methoxy, $CO_2R^{77}$, cyano, nitro, CHO, $CONR^{99}R^{100}$, $CON(OCH_3)CH_3$, or $C_{1-2}$alkyl, heteroaryl, or $C_{3-7}$cycloalkyl optionally substituted with 1-5 independent halogen, hydroxy, cyano, methoxy, —$NHCO_2CH_3$, or —$N(C_{0-2}alkyl)(C_{0-2}alkyl)$ substituents; or $R^3$ and $R^4$ together form a 5-8-membered aromatic, heteroaromatic, carbocyclic, or heterocyclic ring;

$R^5$ and $R^6$ each independently are hydrogen, hydroxy, halogen, cyano, nitro, $CO_2R^7$, CHO, $COR^8$, $C(OH)R^7R^8$, $C(=NOR^7)R^8$, $CONR^9R^{10}$, $SR^7$, $SOR^8$, $SO_2R^8$, $SO_2NR^9R^{10}$, $CH_2NR^9R^{10}$, $NR^9R^{10}$, $N(C_{0-4}alkyl)SO_2R^8$, $NHCOR^7$, or $C_{1-4}$alkyl group, $C_{2-4}$alkenyl group, $C_{2-4}$alkynyl group, $C_{1-4}$alkoxy group, aryl group, or heteroaryl group, wherein any group optionally is substituted with 1-6 independent halogen, cyano, nitro, hydroxy, $C_{1-2}$alkoxy, —$N(C_{0-2}alkyl)(C_{0-2}alkyl)$, $C_{1-2}$alkyl, $CF_nH_{3-n}$, aryl, heteroaryl, —$COC_{1-2}$alkyl, —$CON(CO_2alkyl)(C_{0-2}alkyl)$, $SCH_3$, $SOCH_3$, $SO_2CH_3$, or —$SO_2N(C_{0-2}alkyl)(C_{0-2}alkyl)$ substituents; or $R^5$ and $R^6$ together form a 5-8-membered carbocyclic or heterocyclic ring;

$R^7$ and $R^{77}$ each independently are hydrogen, or $C_{1-4}$alkyl group, $C_{2-4}$alkenyl group, $C_{2-4}$alkynyl group, $C_{3-7}$cycloalkyl group, aryl group, heteroaryl group, or 4-7-membered heterocyclic group, wherein any group optionally is substituted with 1-6 independent halogen, cyano, nitro, hydroxy, $C_{1-2}$alkoxy, —$N(C_{0-2}alkyl)(C_{0-2}alkyl)$, $C_{1-2}$alkyl, $C_{3-7}$cycloalkyl, 4-7-membered heterocyclic ring, $CF_nH_{3-n}$, aryl, heteroaryl, $CO_2H$, —$COC_{1-2}$alkyl, —$CON(C_{0-2}alkyl)(C_{0-2}alkyl)$, $SOCH_3$, $SO_2CH_3$, or —$SO_2N(C_{0-2}alkyl)(C_{0-2}alkyl)$ substituents;

$R^8$ is $C_{1-4}$alkyl group, $C_{2-4}$alkenyl group, $C_{2-4}$alkynyl group, $C_{3-7}$cycloalkyl group, aryl group, heteroaryl group, or 4-7-membered heterocyclic group, wherein any group optionally is substituted with 1-6 independent halogen, cyano, nitro, hydroxy, $C_{1-2}$alkoxy, —$N(C_{0-2}alkyl)(C_{0-2}alkyl)$, $C_{1-2}$alkyl, $C_{3-7}$cycloalkyl, 4-7-membered heterocyclic ring, $CF_nH_{3-n}$, aryl, heteroaryl, $CO_2H$, —$COC_{1-2}$alkyl, —$CON(C_{0-2}alkyl)(CO_2alkyl)$, $SOCH_3$, $SO_2CH_3$, or —$SO_2N(C_{0-2}alkyl)(C_{0-2}alkyl)$ substituents;

$R^9$, $R^{10}$, $R^{99}$, and $R^{100}$ each independently are hydrogen, or $C_{1-4}$alkyl group, $C_{3-7}$cycloalkyl group, aryl group, heteroaryl group, or 4-7-membered heterocyclic group, wherein any group optionally is substituted with 1-6 independent halogen, cyano, nitro, hydroxy, $C_{1-2}$alkoxy, —$N(C_{0-2}alkyl)(C_{0-2}alkyl)$, $C_{1-2}$alkyl, $C_{3-7}$cycloalkyl, 4-7-membered heterocyclic ring, $CF_nH_{3-n}$, aryl, heteroaryl, —$COC_{1-2}$alkyl, —$CON(C_{0-2}alkyl)(C_{0-2}alkyl)$, $SOCH_3$, $SO_2CH_3$, or —$SO_2N(C_{0-2}alkyl)(C_{0-2}alkyl)$ substituents; or $R^9$ and $R^{10}$ or $R^{99}$ and $R^{100}$ together form a 6-8-membered heterobicyclic ring system or a 4-8-membered heterocyclic ring which optionally is substituted with 1-2 independent $C_{1-2}$alkyl, $CH_2OCH_3$, $COC_{0-2}$alkyl, hydroxy, or $SO_2CH_3$ substituents;

n is 1, 2 or 3;

m is 0 or 1;

the dotted line together with the solid line forms an optional double bond, and Δ indicates that the double bond has the (E)-configuration; and with the proviso that Formula (I) does not represent 3-cyclopentyl-2-pyridin-4-yl-N-thiazol-2-ylpropionamide.

If the dotted line together with the solid line forms a single bond, the carbon atom linking the aryl ring and Q-bearing sidechain to the carbonyl carbon is a chiral centre. Accordingly, the compound may be present either as a racemate or as a single enantiomer in the (R)- or (S)-configuration. The (R)-enantiomers are preferred.

In the first aspect, the present invention is directed to a compound represented by Formula (Ia):

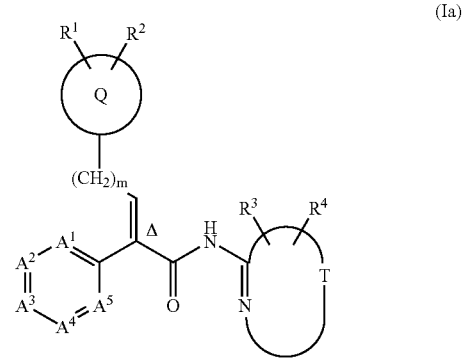

(Ia)

or a pharmaceutically acceptable salt or N-oxide thereof, wherein $A^1$—$A^5$, Q, T, $R^1$—$R^4$, m and Δ are as defined above in Formula (I).

In an embodiment of the first aspect, the present invention is directed to a compound represented by Formula (Ia), or a pharmaceutically acceptable salt or N-oxide thereof, wherein:

$A^3$ is C—$R^5$, $A^4$ is C—$R^6$, one of $A^1$, $A^2$ and $A^5$ is N, and the other two are CH.

In another embodiment of the first aspect, the present invention is directed to a compound represented by Formula (Ia), or a pharmaceutically acceptable salt or N-oxide thereof, wherein:

$A^3$ is C—$R^5$, $A^4$ is C—$R^6$, one of $A^1$, $A^2$ and $A^5$ is N, and the other two are CH;

Q is a $C_{3-8}$cycloalkyl ring.

In another embodiment of the first aspect, the present invention is directed to a compound represented by Formula (Ia), or a pharmaceutically acceptable salt or N-oxide thereof, wherein:

$A^3$ is C—$R^5$, $A^4$ is C—$R^6$, one of $A^1$, $A^2$ and $A^5$ is N, and the other two are CH;

Q is a 4-8-membered heterocyclic ring.

In another embodiment of the first aspect, the present invention is directed to a compound represented by Formula (Ia), or a pharmaceutically acceptable salt or N-oxide thereof, wherein:

$A^3$ is C—$R^5$, $A^4$ is N, one of $A^1$, $A^2$ and $A^5$ is N, and the other two are CH.

In another embodiment of the first aspect, the present invention is directed to a compound represented by Formula (Ia), or a pharmaceutically acceptable salt or N-oxide thereof, wherein:

$A^3$ is C—$R^5$, $A^4$ is N, one of $A^1$, $A^2$ and $A^5$ is N, and the other two are CH;

Q is a $C_{3-8}$cycloalkyl ring.

In the second aspect, the present invention is directed to a compound represented by Formula (Ib):

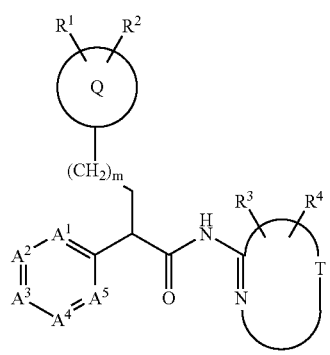

(Ib)

or a pharmaceutically acceptable salt or N-oxide thereof, wherein $A^1$—$A^5$, Q, T, $R^1$—$R^4$ and m are as defined above in Formula (I).

In an embodiment of the second aspect, the present invention is directed to a compound represented by Formula (Ib), or a pharmaceutically acceptable salt or N-oxide thereof, wherein:

$A^3$ is C—$R^5$, $A^4$ is C—$R^6$, one of $A^1$, $A^2$ and $A^5$ is N, and the other two are CH.

In another embodiment of the second aspect, the present invention is directed to a compound represented by Formula (Ib), or a pharmaceutically acceptable salt or N-oxide thereof, wherein:

$A^3$ is C—$R^5$, $A^4$ is C—$R^6$, one of $A^1$, $A^2$ and $A^5$ is N, and the other two are CH;

Q is a $C_{3-8}$cycloalkyl ring.

The molecular weight of the compounds of Formula (I) is preferably less than 800, more preferably less than 600, most preferably less than 500.

In the present invention, $A^1$ and $A^5$ are preferably CH.

In the present invention, $A^2$ is preferably N.

In the present invention, $A^3$ is preferably $CR^5$.

In the present invention, $A^4$ is preferably C—$R^6$ or N; more preferably C—$R^6$.

In the present invention, Q is preferably cyclopentyl, cyclohexyl, tetrahydropyranyl, tetrahydrothiopyranyl, 1-oxo-tetrahydrothiopyranyl or 1,1-dioxo-tetrahydrothiopyranyl; more preferably cyclopentyl, cyclohexyl, 4-tetrahydropyranyl, or 4-tetrahydrothiopyranyl; most preferably cyclopentyl or cyclohexyl.

When Q is a heteroaryl or heterocyclic group it is preferably linked to the —$(CH_2)_m$— group through a carbon atom.

When Q is a heteroaryl group it preferably does not have a substituent $R^1$ or $R^2$ other than hydrogen at a position adjacent to point of attachment to the —$(CH_2)_m$— group.

In the present invention, the group of formula

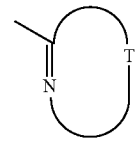

is preferably a monocyclic heteroaryl group. More preferably it is thiazolyl, thiadiazolyl, oxazolyl, isoxazolyl, pyrimidinyl, pyrazinyl, or pyridyl; more preferably 2-thiazolyl, 5-[1,2,4]thiadiazolyl, 2-[1,3,4]thiadiazolyl, 4-pyrimidinyl, 2-pyrazinyl, 3-isoxazolyl, or 2-pyridyl; most preferably 2-thiazolyl, 5-[1,2,4]thiadiazolyl, or 2-pyridyl.

More preferably the group of formula

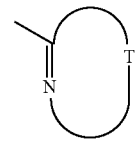

is 2-thiazolyl, e.g. 2-thiazolyl where $R^3$ is 5-halo such as 5-fluoro, and $R^4$ is hydrogen.

In the present invention, $R^1$ and $R^2$ are preferably hydrogen.

In the present invention, $R^3$ is preferably hydrogen, halogen, $C_{1-2}$alkyl, or trifluoromethyl; more preferably hydrogen, methyl, fluoro, chloro or bromo; even more preferably hydrogen, fluoro, or chloro; most preferably hydrogen or fluoro.

In the present invention, $R^4$ is preferably hydrogen or methyl; more preferably hydrogen.

In the present invention, $R^5$ is preferably $CF_3$, $SOR^8$, $SO_2R^8$, $SO_2NR^9R^{10}$, $NHSO_2R^8$, triazolyl, or tetrazolyl; more preferably $SOR^8$, $SO_2R^8$, $SO_2NR^9R^{10}$, or $NHSO_2R^8$; most preferably $SOR^8$ or $SO_2R^8$.

In the present invention, $R^6$ is preferably hydrogen, chloro, fluoro, or trifluoromethyl; more preferably hydrogen.

In the present invention, $R^7$, $R^{77}$, and $R^8$ are preferably $C_{1-4}$alkyl, $C_{3-7}$cycloalkyl, heteroaryl, or 4-8-membered heterocyclic group; more preferably $C_{1-4}$alkyl or $C_{3-7}$cycloalkyl.

In the present invention, $R^9$ and $R^{10}$ are preferably $C_{0-4}$alkyl or combine to form a 4-8-membered heterocyclic ring.

In the present invention, $R^{99}$ and $R^{100}$ are preferably $C_{0-4}$alkyl.

In the present invention, m is preferably 0.

In the present invention, n is preferably 2 or 3.

Specific compounds of the invention which may be mentioned are those described in the Examples and pharmaceutically acceptable salts or N-oxides thereof.

While the preferred groups for each variable have generally been listed above separately for each variable, preferred compounds of this invention include those in which several or each variable in Formula (I) is selected from the preferred, more preferred, most preferred, especially or particularly listed groups for each variable. Therefore, this invention is intended to include all combinations of preferred, more preferred, most preferred, especially and particularly listed groups.

As used herein, unless stated otherwise, "alkyl" as well as other groups having the prefix "alk" such as, for example, alkoxy, alkanyl, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

As used herein, for example, "$C_{0-4}$alkyl" is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

The terms "cycloalkyl" and "carbocyclic ring" mean carbocycles containing no heteroatoms, and include mono-, bi-, and tricyclic saturated carbocycles, as well as fused and bridged systems. Such fused ring systems can include one ring that is partially or fully unsaturated, such as a benzene ring, to form fused ring systems, such as benzofused carbocycles. Cycloalkyl includes such fused ring systems as spirofused ring systems. Examples of cycloalkyl and carbocyclic rings include $C_{3-8}$cycloalkyl such as cyclopropyl, cyclobutyl, cyclopentyl, cyclohexyl, and decahydronaphthalene, adamantane, indanyl, 1,2,3,4-tetrahydronaphthalene and the like.

The term "halogen" includes fluorine, chlorine, bromine, and iodine atoms.

The term "aryl" includes, for example, phenyl and naphthyl.

Unless otherwise stated, the term "heterocyclic ring" includes 48-membered saturated rings containing one or two heteroatoms chosen from oxygen, sulfur, and nitrogen. The heteroatoms are not directly attached to one another. Examples of heterocyclic rings include oxetane, tetrahydrofuran, tetrahydropyran, oxepane, oxocane, thietane, tetrahydrothiophene, tetrahydrothiopyran, thiepane, thiocane, azetidine, pyrrolidine, piperidine, azepane, azocane, [1,3] dioxane, oxazolidine, piperazine, and the like. Other examples of heterocyclic rings include the oxidised forms of the sulfur-containing rings. Thus, tetrahydrothiophene 1-oxide, tetrahydrothiophene 1,1-dioxide, tetrahydrothiopyran 1-oxide, and tetrahydrothiopyran 1,1-dioxide are also considered to be heterocyclic rings.

Unless otherwise stated, the term "heteroaryl" includes 5- or 6-membered heteroaryl rings containing 14 heteroatoms chosen from oxygen, sulfur, and nitrogen. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, or triazinyl.

The above formulas are shown without a definitive stereochemistry at certain positions. The present invention includes all stereoisomers (e.g. geometric isomers, optical isomers, diastereoisomers, etc.) and pharmaceutically acceptable salt or N-oxides thereof, except where specifically drawn or stated otherwise. Further, mixtures of stereoisomers as well as isolated specific stereoisomers are also included, except where specifically drawn or stated otherwise. During the course of the synthetic procedures used to prepare such compounds, or in using racemization or epimerization procedures known to those skilled in the art, the products of such procedures can be a mixture of stereoisomers. When a tautomer of the compound of the above formulas exists, the present invention includes any possible tautomers and pharmaceutically acceptable salts or N-oxides thereof, and mixtures thereof, except where specifically drawn or stated otherwise. When the compound of the above formulas and pharmaceutically acceptable salts or N-oxides thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

Since the compounds of formula (I) are intended for pharmaceutical use they are preferably provided in substantially pure form, for example at least 60% pure, more suitably at least 75% pure, especially at least 98% pure (% are on a weight for weight basis).

The invention also encompasses a pharmaceutical composition that is comprised of a compound of Formula (I), or a pharmaceutically acceptable salt or N-oxide thereof, in combination with a pharmaceutically acceptable carrier.

Preferably the composition is comprised of a pharmaceutically acceptable carrier and a non-toxic therapeutically effective amount of a compound of Formula (I) as described above, or a pharmaceutically acceptable salt or N-oxide thereof.

Moreover, within this preferred embodiment, the invention encompasses a pharmaceutical composition for the prophylaxis or treatment of hyperglycemia and diabetes by the activation of GK, comprising a pharmaceutically acceptable carrier and a non-toxic therapeutically effective amount of compound of Formula (I) as described above, or a pharmaceutically acceptable salt or N-oxide thereof.

The compounds and compositions of the present invention are effective for treating hyperglycemia in mammals such as, for example, humans.

The invention also provides a method of prophylactic or therapeutic treatment of a condition where activation of GK is desirable comprising a step of administering an effective amount of a compound of Formula (I), or a pharmaceutically acceptable salt thereof.

The invention also provides a method of prophylactic or therapeutic treatment of hyperglycemia or diabetes comprising a step of administering an effective amount of a compound of Formula (I), or a pharmaceutically acceptable salt thereof.

The invention also provides a method of prevention of diabetes in a human demonstrating pre-diabetic hyperglycemia or impaired glucose tolerance comprising a step of administering an effective prophylactic amount of a compound of Formula (I), or a pharmaceutically acceptable salt thereof.

The invention also provides the use of a compound of Formula (I), or a pharmaceutically acceptable salt thereof, as a GK activator.

The invention also provides the use of a compound of Formula (I), or a pharmaceutically acceptable salt thereof, for the prophylactic or therapeutic treatment of hyperglycemia or diabetes.

The invention also provides the use of a compound of Formula (I), or a pharmaceutically acceptable salt thereof, for the prevention of diabetes in a human demonstrating pre-diabetic hyperglycemia or impaired glucose tolerance.

The invention also provides the use of a compound of Formula (I), or a pharmaceutically acceptable salt thereof, in the manufacture of a medicament for the activation of GK.

The invention also provides the use of a compound of Formula (I), or a pharmaceutically acceptable salt thereof, in the manufacture of a medicament for the prophylactic or therapeutic treatment of hyperglycemia or diabetes.

The invention also provides the use of a compound of Formula (I), or a pharmaceutically acceptable salt thereof, in the manufacture of a medicament for the prevention of diabetes in a human demonstrating pre-diabetic hyperglycemia or impaired glucose tolerance.

The compounds and compositions of the present invention may be optionally employed in combination with one or more other anti-diabetic agents or anti-hyperglycemic agents, which include, for example, sulfonylureas (e.g. glyburide, glimepiride, glipyride, glipizide, chlorpropamide, gliclazide, glisoxepid, acetohexamide, glibomuride, tolbutamide, tolazamide, carbutamide, gliquidone, glyhexamide, phenbutamide, tolcyclamide, etc.), biguanides (e.g. metformin, phenformin, buformin, etc.), glucagon antagonists (e.g. a peptide or non-peptide glucagon antagonist), glucosidase inhibitors (e.g. acarbose, miglitol, etc.), insulin secetagogues, insulin sensitizers (e.g. troglitazone, rosiglitazone, pioglitazone, etc.) and the like; or anti-obesity agents (e.g. sibutramine, orlistat, etc.) and the like. The compounds and compositions of the present invention and the other anti-diabetic agents or anti-hyperglycemic agents may be administered simultaneously, sequentially or separately.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthetic amines. Other pharmaceutically acceptable organic non-toxic bases from which salts can be formed include, for example, arginine, betaine, caffeine, choline, N',N'-dibenzylethylenediamine, diethylamine, 2-diethylaminoethanol, 2-dimethylaminoethanol, ethanolamine, ethylenediaamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, methanesulfonic, and tartaric acids.

The pharmaceutical compositions of the present invention comprise a compound represented by Formula (I), or a pharmaceutically acceptable salt or N-oxide thereof, as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, as well as administration through inhaling, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The pharmaceutical compositions according to the invention are preferably adapted for oral administration.

In practice, the compounds represented by Formula (I), or pharmaceutically acceptable salts or N-oxides thereof, of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula (I), or a pharmaceutically acceptable salt or N-oxide thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound of Formula (I), or a pharmaceutically acceptable salt or N-oxide thereof. The compounds of Formula (I), or pharmaceutically acceptable salts or N-oxides thereof, can also be included in pharmaceutical compositions in combination with one or more other therapeutically active compounds.

The pharmaceutical compositions of this invention include a pharmaceutically acceptable liposomal formulation containing a compound of Formula (I) or a pharmaceutically acceptable salt or N-oxide thereof.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent or other such excipient. These excipients may be, for example, inert diluents such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer time. For example, a time delay material such as glyceryl monostearate or glyceryl distearate may be used.

In hard gelatin capsules, the active ingredient is mixed with an inert solid diluent, for example, calcium carbonate, calcium phosphate or kaolin. In soft gelatin capsules, the active ingredient is mixed with water or an oil medium, for example, peanut oil, liquid paraffin or olive oil. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound of Formula (I), or a pharmaceutically acceptable salt or N-oxide thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

Pharmaceutical compositions of this invention can be in a form suitable for inhaled administration. Such administration can be in forms and utilizing carriers described in, for example, 1) *Particulate Interactions in Dry Powder Formulations for Inhalation*, Xian Zeng et al., 2000, Taylor and Francis, 2) *Pharmaceutical Inhalation Aerosol Technology*, Anthony Hickey, 1992, Marcel Dekker, 3) *Respiratory Drug Delivery*, 1990, Editor: P. R. Byron, CRC Press.

In addition to the aforementioned carrier ingredients, the pharmaceutical compositions described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of Formula (I), or pharmaceutically acceptable salts or N-oxides thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 10 g per patient per day. For example, diabetes may be effectively treated by the administration of from about 0.01 to 100 mg of the compound per kilogram of body weight per day, or alternatively about 0.5 mg to about 7 g per patient per day.

It is understood, however, that the specific dose level for any particular patient will depend upon a variety of factors including the age, body weight, general health, sex, diet, time of administration, route of administration, rate of excretion, drug combination and the severity of the disease in the particular diabetic patient undergoing therapy. Further, it is understood that the compounds and salt or N-oxides thereof of this invention can be administered at subtherapeutic levels prophylactically in anticipation of a hyperglycemic condition.

It is known in the field of diabetes that persons likely to develop diabetes typically demonstrate impaired glucose tolerance or demonstrate hyperglycemia. Thus, the compounds of the present invention, or pharmaceutically acceptable salts or N-oxides thereof, can be administered in prophylactically effective amounts to prevent the onset of diabetes. Accordingly, the present invention includes a method of treatment of hyperglycemia by administering an effective amount—and a method of prevention of diabetes in a human demonstrating pre-diabetic hyperglycemia or impaired glucose tolerance by administering an effective prophylactic amount—of the compound of the present invention, or a pharmaceutically acceptable salt or N-oxide thereof.

The compounds of Formula (I) may exhibit advantageous properties compared to known GK activators.

Experimental

In accordance with this invention, the α,β-unsaturated enamides of Formula (Ia) can be prepared following the protocol illustrated in Scheme 1 below:

wherein:

$A^1$—$A^5$, Q, T, $R^1$—$R^4$, m and Δ are as described above;

$R^{11}$ is $C_1$-$C_4$ alkyl; and $X^1$ and $X^2$ each independently are bromo or iodo.

The 2-haloacrylate esters II are readily prepared by halogenation of the syn addition product formed by reaction of an organocopper compound with a lower alkyl ester of propiolic acid (R. Rossi et al., *J Organomet. Chem.*, 1993, 451, 33-43). The halogenated heteroaromatic species III are either commercially available or readily made utilising known synthetic procedures (See, for example: R. N. Guthikonda & F. P. DiNinno, U.S. Pat. No. 5,409,920; X. Wang et al., *Tetrahedron Lett.*, 2000, 41, 4335-4338). Compound II is reacted with activated zinc to generate an alkenylzinc species that is then cross-coupled with the halide III in the presence of a source of palladium(0) in a suitable solvent, such as tetrahydrofuran, at around 40° C. (WO 01/44216). Saponification of the resultant (E)-enoate ester, employing, for example, sodium hydroxide in aqueous methanol at 20° C. to reflux, leads to the (E)-α,β-unsaturated carboxylic acid IV.

The α,β-unsaturated carboxylic acids IV may be condensed with heteroaromatic amines V, many of which are commercially available, using a variety of coupling conditions, e.g. polymer supported carbodiimide-1-hydroxybenzotriazole in N,N-dimethylformamide at 20° C. (for representative procedures, see http://www.argotech.com/PDF/resins/ps_carbodiimide.pdf and available from Argonaut Technologies, Inc., Foster City, Calif.), to give (Ia).

SCHEME 1

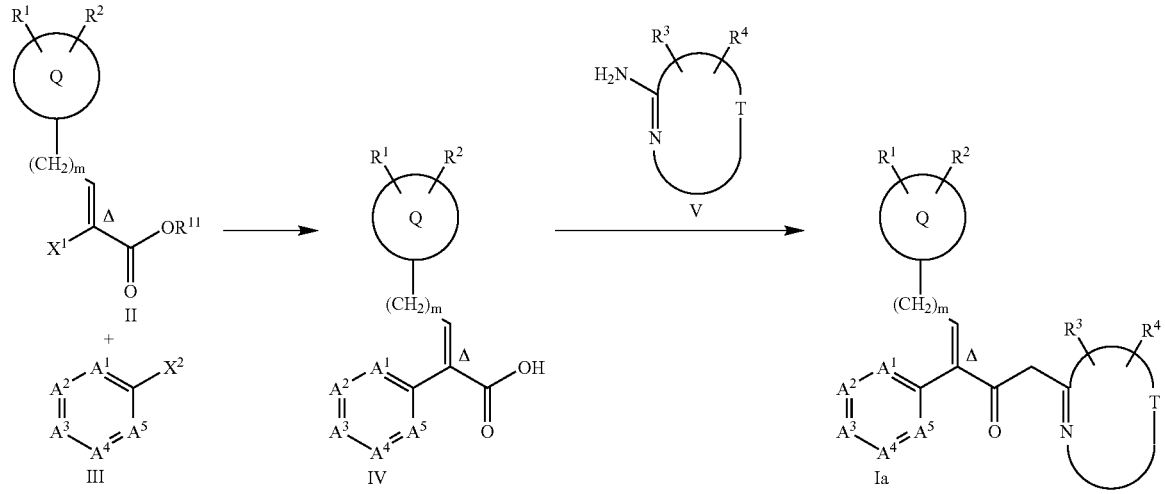

The saturated amides of Formula (Ib) can be made employing the protocol shown in Scheme 2 below:

SCHEME 2

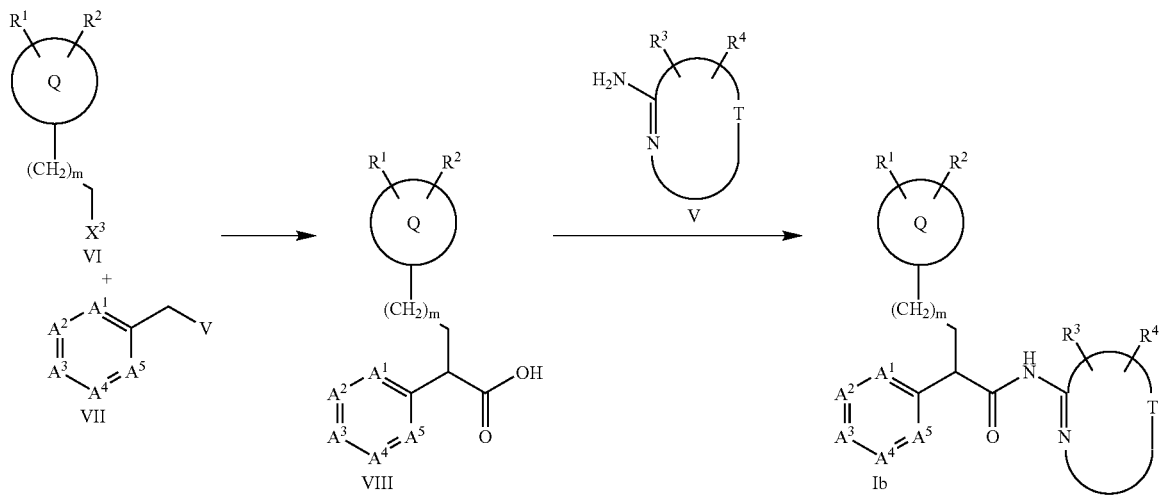

wherein:

$A^1$—$A^5$, Q, T, $R^1$—$R^4$ and m are as described above;

V is $CO_2R^{11}$, $CO_2CH_2Ph$, or CN; and $X^3$ is chloro, bromo, iodo, or $OSO_2R^{12}$;

wherein $R^{11}$ is as described above and $R^{12}$ is $C_1$-$C_4$ alkyl, optionally substituted with one or more fluorines, or optionally substituted aryl.

The halides and sulfonate esters VI are commercially available or are readily prepared using known techniques. These alkylating agents may be reacted with the α-carbanions of acetic esters or acetonitriles VII, generated at −78° C. in tetrahydrofuran by a strong base, such as lithium diisopropylamide (WO 00/58293), to give α-substituted esters and nitriles. The carboxylic acids VIII can be obtained by saponification of the α-substituted esters with, for example, sodium hydroxide in aqueous methanol at 20° C. to reflux and by hydrolysis of the α-substituted nitriles with, for example, aqueous sulfuric acid at elevated temperatures (R. Adams and A. F. Thal, Org. Synth. Coll. Vol. 1, 436).

The carboxylic acids VIII may be condensed with heteroaromatic amines V, many of which are commercially available, using a variety of coupling conditions, e.g. O-(1H-benzotriazol-1-yl)-N,N,N',N'-tetramethyluronium tetrafluoroborate (R. Knorr et al., Tetrahedron Lett., 1989, 30, 1927-1930) in N,N-dimethylformamide at 20° C., to give (Ib).

The compound of Formula (Ib) has an asymmetric carbon atom which interlinks the amide carbonyl carbon, the aryl ring, and the Q-containing sidechain. In accordance with this invention, the preferred stereoconfiguration at the asymmetric centre is (R).

If one desires to isolate the pure (R)- or (S)-stereoisomers of the compound of Formula (Ib), it is possible to resolve a racemic mixture of the chiral carboxylic acid precursor VIII by any conventional chemical means and then condense the enantiopure carboxylic acids with an amine of formula V using a reagent that causes negligible racemisation. By way of illustration, racemic VIII can be condensed with a chiral oxazolidinone derivative (see, for instance, F. T. Bizzarro et al. WO 00/58293) to generate a mixture of diastereoisomeric imides that are separable by any conventional method, e.g. column chromatography. Hydrolysis of the pure imides affords the stereopure (R)- and (S)-carboxylic acids that can then be condensed with heterocyclic amines V, employing a reagent that minimises racemisation of the chiral centre, e.g. benzotriazol-1-yloxytris(pyrrolidino)phosphonium hexafluorophosphate (J. Coste et al. Tetrahedron Lett. 1990, 31, 205-208), to furnish enantiopure (R)- or (S)-amides of Formula (Ib). Alternatively, a racemic mixture of amides of Formula (Ib) can be separated by means of chiral high performance liquid chromatography employing a chiral stationary phase which can be purchased from, for example, Daicel Chemical Industries, Ltd, Tokyo, Japan. Further details for the preparation of the compounds of Formula (I) are found in the examples.

The compounds of Formula (I) may be prepared singly or as compound libraries comprising at least 2, for example 5 to 1,000, compounds and more preferably 10 to 100 compounds of Formula (I). Compound libraries may be prepared by a combinatorial "split and mix" approach or by multiple parallel synthesis using either solution or solid phase chemistry, using procedures known to those skilled in the art.

During the synthesis of the compounds of Formula (I), labile functional groups in the intermediate compounds, e.g. hydroxy, carboxy and amino groups, may be protected. The protecting groups may be removed at any stage in the synthesis of the compounds of Formula (I) or may be present on the final compound of Formula (I). A comprehensive discussion of the ways in which various labile functional groups may be protected and methods for cleaving the resulting protected derivatives is given in, for example, Protective Groups in Organic Chemistry, T. W. Greene and P. G. M. Wuts, (1991) Wiley-Interscience, New York, $2^{nd}$ edition.

Any novel intermediates as defined above are also included within the scope of the invention.

According to a further aspect of the invention there is provided a compound of Formula (IV):

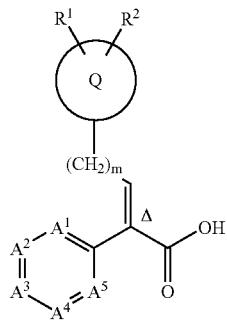

wherein $A^1$—$A^5$, Q, $R^1$, $R^2$, m and Δ are as described for Formula (I).

According to a further aspect of the invention there is provided a compound of Formula (VIII):

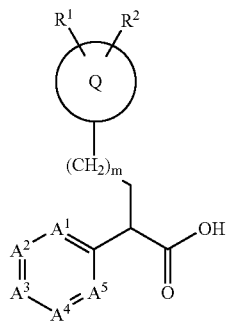

wherein $A^1$—$A^5$, Q, $R^1$, $R^2$ and m are as described for Formula (I).

The preferences for the various substituent groups in the compounds of Formulae (IV) and (VIII) are as described above for the compounds of Formula (I).

Specific compounds of Formulae (IV) and (VIII) include those described in the Preparations.

All publications, including, but not limited to, patents and patent application cited in this specification, are herein incorporated by reference as if each individual publication were specifically and individually indicated to be incorporated by reference herein as fully set forth.

Materials and Methods

Microwave reactions were performed in a CEM Explorer system at 100 W. Column chromatography was carried out on $SiO_2$ (40-63 mesh). LCMS data were obtained employing one of two methods: Method A: Waters Symmetry 3.5μ $C_{18}$ column (2.1×30.0 mm, flow rate=0.8 mL $min^{-1}$) eluting with a (5% MeCN in $H_2O$)—MeCN solution containing 0.1% $HCO_2H$ over 6 min and UV detection at 220 nm. Gradient information: 0.0-1.2 min: 100% (5% MeCN in $H_2O$); 1.2-3.8 min: Ramp up to 10% (5% MeCN in $H_2O$)–90% MeCN; 3.8-4.4 min: Hold at 10% (5% MeCN in $H_2O$)–90% MeCN; 4.4-5.5 min: Ramp up to 100% MeCN; 5.5-6.0 min: Return to 100% (5% MeCN in $H_2O$). Method B: Phenomenex Mercury Luna 3μ $C_{18}$ column (2.0×10.0 mm, flow rate=1.5 mL/min), eluting with a (5% MeCN in $H_2O$)—MeCN solution (4:1 to 1:4) containing 0.1% $HCO_2H$ over 2.95 min, & employing diode array detection. The mass spectra for both Methods A and B were obtained employing an electrospray ionisation source in either the positive ion ($ES^+$) or negative ion ($ES^-$) mode. Atmospheric Pressure Chemical Ionisation (APCI) spectra were obtained on a FinniganMat SSQ 7000C instrument. The syntheses of the following compounds have been reported previously: Bis(tert-butyl)(5-bromo-2-pyridinyl)imidodicarbonate: D. J. P. Pinto et al., U.S. Pat. No. 6,020,357; 5-Bromo-2,3-dichloropyridine: EP 0136593; 5-Bromo-2-ethylsulfanylpyridine: WO 01/44243; 2-Bromo-5-methylsulfanylpyridine: WO 01/64669; 5-Bromo-2-methylsulfanylpyridine: X. Wang et al., *Tetrahedron Lett.* 2000, 41, 4335-4338; N-(5-Bromopyridin-2-yl)acetamide: M. Sollogoub et al., *Tetrahedron Lett.* 2002, 43, 3121-3123; 5-Bromo-2-[1,2,4]triazol-1-ylpyridine: WO 01/94342; tert-Butyl (5-bromopyridin-2-yl)methylcarbamate: WO 99/30709; (6-Chloropyridin-3-yl)acetonitrile: WO 01/83475; Cyclopentylmethyltriphenylphosphonium iodide: WO 01/44216; Dicyclopropyldisulfide: E. Block et al., *J. Am. Chem. Soc.* 1992, 114, 3492-3499; (Z)-Methyl 3-cyclopentyl-2-iodoacrylate: WO 01/44216.

Abbreviations and acronyms: Ac: Acetyl; ATP: Adenosine 5'-triphosphate; BINAP: 2,2'-Bis(diphenylphosphino)-1,1'-binaphthyl; n-Bu: n-Butyl; dba: dibenzylideneacetone; DBE: 1,2-dibromoethane; DMF: N,N-Dimethylformamide; DMSO: Dimethylsulfoxide; EDCI: 1-(3-Dimethylaminopropyl)-3-ethylcarbodiimide hydrochloride; Et: Ethyl; FA: Fold activation; GK: Glucokinase; Glc: Glucose; G6P: Glucose-6-phosphate; G6PDH: Glucose-6-phosphate dehydrogenase; GST-GK: Glutathione S-transferase-Glucokinase fusion protein; HMPA: Hexamethylphosphoramide; HOBt: 1-Hydroxybenzotriazole; IH: Isohexane; KHMDS: Potassium bis(trimethylsilyl)amide; LDA: Lithium diisopropylamide; LHMDS: Lithium bis(trimethylsilyl)amide; mCPBA: 3-Chloroperoxybenzoic acid; Me: Methyl; Ms: Methanesulfonyl; NADP(H): β-Nicotinamide adenine dinucleotide phosphate (reduced); Ph: Phenyl; n-Pr: n-Propyl; PS: Polymer supported; RP-HPLC: Reverse-phase high-pressure liquid chromatography; RT: Retention time; $RT^A$: Retention time with Method A; $RT^B$: Retention time with Method B; TBTU: O-(1H-Benzotriazol-1-yl)-N,N,N',N'-tetramethyluronium tetrafluoroborate; Tf: Trifluoromethanesulfonyl; TFA: Trifluoroacetic acid; TFAA: Trifluoroacetic anhydride; THF: Tetrahydrofuran; TMSCl: Chlorotrimethylsilane.

Preparation 1: 2-(6-Chloropyridin-3-yl)-3-cyclopentylpropionic Acid

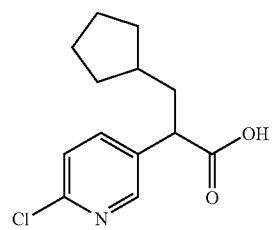

Step 1: KHMDS (30.9 mL of a 1 mmol $mL^{-1}$ solution in THF, 30.9 mmol) was added to a stirred solution of (6-chloropyridin-3-yl)acetonitrile (4.40 g, 28.9 mmol) in anhydrous THF-HMPA (3:1, 72 mL) at −78° C. After 30 min, iodomethylcyclopentane (1.46 g, 6.9 mmol) was added. The solution was stirred at −78° C. for 4.5 h, before being allowed to warm to 20° C. over 16 h. The reaction mixture was carefully quenched with saturated aqueous $NH_4Cl$ (20 mL), then $H_2O$ (100 mL) was added. The mixture was extracted with EtOAc (3×50 mL), then the extracts were dried (Na$_2$SO$_4$). Filtration, solvent evaporation, and column chromatography (n-C$_6$H$_{14}$-EtOAc) furnished 2-(6-chloropyridin-3-yl)-3-cyclopentylpropionitrile: m/z (ES$^+$)=235.1 [M+H]$^+$. Step 2: This compound (2.30 g, 9.8 mmol) was heated with 50% aqueous H$_2$SO$_4$ (10 mL) at 130° C. for 2 h with stirring. The mixture was allowed to cool down to 20° C. over 16 h, before being neutralised with saturated aqueous Na$_2$CO$_3$ and extracted with CHCl$_3$. The organic extracts were dried (Na$_2$SO$_4$), before being filtered and concentrated to give the title compound: m/z (ES$^+$)=254.2 [M+H]$^+$.

Preparation 2: 3-Cyclopentyl-2-pyridin-3-ylpropionic Acid

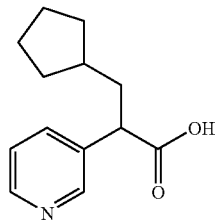

Step 1: LDA (50.1 mL of a 1.5 mmol mL-1 solution in c-C$_6$H$_{12}$, 7.6 mmol) was added to a stirred solution of ethyl 3-pyridylacetate (1.15 g, 6.9 mmol) in anhydrous THF-HMPA (3:1, 260 mL) at −78° C. After 30 min, iodomethylcyclopentane (1.46 g, 6.9 mmol) was added, then stirring was continued at −78° C. for 4.5 h. The mixture was allowed to warm to 20° C., before being stirred for 16 h. The reaction mixture was carefully quenched with saturated aqueous NH$_4$Cl (20 mL), then H$_2$O (100 mL) was added. The mixture was extracted with EtOAc (3×50 mL), then the extracts were dried (Na$_2$SO$_4$). Filtration, solvent evaporation, and column chromatography (n-C$_6$H$_4$-EtOAc) furnished ethyl 3-cyclopentyl-2-pyridin-3-ylpropionate: m/z (ES$^+$)=248.3 [M+H]$^+$. Step 2: A stirred solution of this compound (0.73 g, 3.0 mmol) in THF (3 mL) was treated with 2M NaOH (3 mL, 6.0 mmol). After 16 h at 20° C., the organic solvent was removed under reduced pressure, then the pH of the remaining solution was adjusted to 6.5, before being extracted with EtOAc. The EtOAc extracts were dried (Na$_2$SO$_4$), filtered, and concentrated to give the title compound: m/z (ES$^+$)=220.2 [M+H]$^+$.

Preparation 3: (E)-3-Cyclopentyl-2-(6-methylsulfanylpyridin-3-yl)acrylic Acid

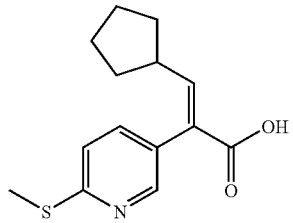

Step 1: DBE (345 μL, 4.0 mmol) was added to a suspension of Zn dust (2.62 g, 40.0 mmol) in anhydrous THF (4 mL). The mixture was heated to boiling, then allowed to cool down to 20° C. This process was repeated three times, then the mixture was stirred at 20° C. for 2 h, before being treated with TMSCl (380 μL, 3.0 mmol). Stirring was continued for 1.5 h, then a solution of (Z)-methyl 3-cyclopentyl-2-iodoacrylate (2.52 g, 9.0 mmol) in anhydrous THF (8 mL) was added over 3 min. The mixture was stirred at 40° C. for 2 h, before being stirred at 20° C. for 16 h, and finally allowed to stand for 4 h. In a separate reaction vessel, a solution of PPh$_3$ (315 mg, 1.2 mmol) and Pd$_2$(dba)$_3$ (150 mg, 0.5 mmol) in anhydrous THF (15 mL) was stirred for 2 h at 20° C., before being treated with a solution of 5-bromo-2-methylsulfanylpyridine (2.76 g, 13.5 mmol) in anhydrous THF (10 mL). The solution of the freshly prepared organozinc compound was then added via cannula, and the mixture was stirred at 40° C. for 68 h. Solvent evaporation and column chromatography (4:1 IH-Et$_2$O) yielded methyl 3-cyclopentyl-2-(6-methylsulfanylpyridin-3-yl)acrylate: m/z (ES$^+$)=278.1 [M+H]$^+$. Step 2: A solution of this compound (1.12 g, 4.0 mmol) in MeOH (5.5 mL) was treated with 1M NaOH (8.9 mL, 8.9 mmol). The mixture was heated at 65° C. for 3 h, before being stirred at 20° C. for 16 h. The MeOH was removed under reduced pressure, then H$_2$O (10 mL) and 1M NaOH (10 mL) were added. The resulting mixture was washed with Et$_2$O (25 mL), before being acidified with 2M HCl to adjust the pH to 1. The suspension produced was extracted with EtOAc (2×50 mL), then the extracts were washed with brine (20 mL), before being dried (MgSO$_4$). Filtration, solvent evaporation, and recrystallisation (EtOAc-IH) furnished the title compound: m/z (ES$^+$)=264.1 [M+H]$^+$.

The compounds listed in TABLE 1 were prepared from (Z)-methyl 3-cyclopentyl-2-iodoacrylate and the appropriate heteroaryl bromide employing the protocol described in Preparation 3, unless noted otherwise.

TABLE 1

| Prep | Structure | Name | m/z (ES$^+$) |
| --- | --- | --- | --- |
| 4 | 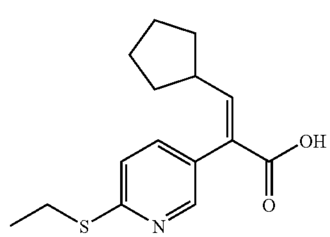 | (E)-3-Cyclopentyl-2-(6-ethylsulfanylpyridin-3-yl)acrylic acid | 278.0 [M + H]$^+$ |

TABLE 1-continued

| Prep | Structure | Name | m/z (ES+) |
|---|---|---|---|
| 5 | 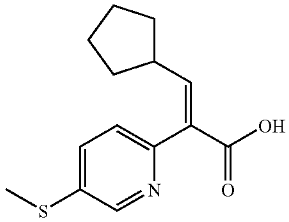 | (E)-3-Cyclopentyl-2-(5-methylsulfanylpyridin-2-yl)acrylic acid | 264.0 [M + H]+ |
| 6 | 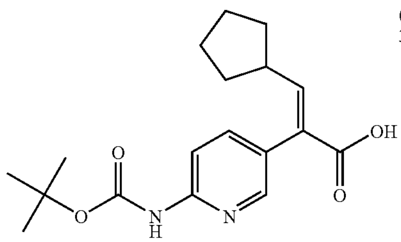 | (E)-2-(6-tert-Butoxycarbonylaminopyridin-3-yl)-3-cyclopentylacrylic acid | 333.3 [M + H]+. |
| 7[a] | 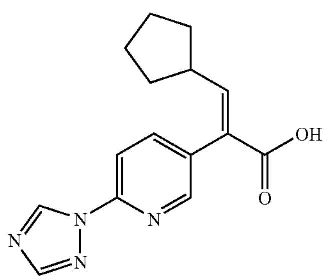 | (E)-3-cyclopentyl-2-(6-[1,2,4]triazol-1-ylpyridin-3-yl)acrylic acid | 285.1 [M + H]+ |
| 8[a] | 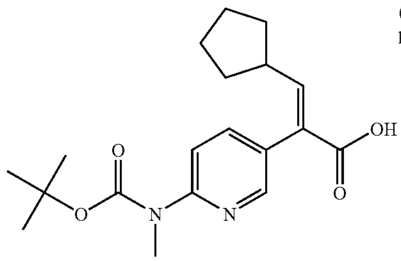 | (E)-2-(6-(tert-Butoxycarbonylmethylamino)-pyridin-3-yl]-3-cyclopentylacrylic acid | 347.2 [M + H]+. |

[a]Prepared using the Pd-catalysed cross-coupling conditions described in Step 2 of Preparation 9.

Preparation 9: (E)-3-Cyclopentyl-2-[6-(5-methyltetrazol-1-yl)pyridin-3-yl]acrylic Acid

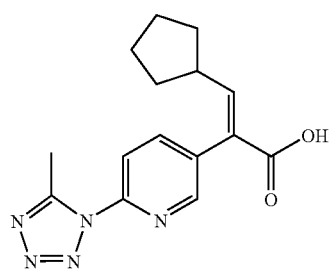

Step 1: NaN$_3$ (13.69 g, 210.6 mmol) and Tf$_2$O (33 mL, 196.5 mmol) were added to a stirred solution of N-(5-bromopyridin-2-yl)acetamide (8.31 g, 38.6 mmol) in anhydrous MeCN (200 mL) at 0° C. After 2.5 h, the temperature was increased to 45° C., then stirring was continued for 16 h. The solvents were evaporated off under reduced pressure, then the remainder was partitioned between CH$_2$Cl$_2$ (250 mL) and saturated aqueous NaHCO$_3$ (250 mL). The aqueous phase was extracted further with CH$_2$Cl$_2$ (250 mL), the the combined organic extracts were washed with H$_2$O (200 mL) and brine (200 mL), before being dried (MgSO$_4$). Filtration and solvent evaporation gave a residue that was purified by flash chromatography (CH$_2$Cl$_2$-THF, 1:0 to 15: 1). A second flash chromatographic purification (1H-EtOAc, 10:1 to 3:2) of the material thus obtained afforded 5-bromo-2-(5-methyltetrazol-1-yl)pyridine: 4 (CDCl$_3$): 2.95 (s, 3H), 7.95 (d, 1H), 8.10 (dd, 1H), 8.65 (d, 1H). Step 2: DBE (310 µL, 3.5 mmol) was added to a suspension of Zn dust (1.49 g, 22.5 mmol) in anhydrous THF (4 mL). The mixture was heated to boiling, then allowed to cool down to 20° C. This process was repeated three times, then TMSCl (300 µL, 2.3 mmol) was added. The reaction was stirred at 20° C. for 70 min, then a solution of (Z)-methyl 3-cyclopentyl-2-iodoacrylate (1.31 g, 5.0 mmol) in anhydrous DMF (6 mL) was added. The mixture was stirred at 45° C. (bath) for 65 min, before being left at 25° C. for 16 h. Anhydrous THF (13 mL) was added, then the mixture was allowed to settle. The organozinc solution was added with stirring to a suspension of Pd(PPh$_3$)$_2$Cl$_2$ (0.38 g, 0.5 mmol) and 5-bromo-2-(5-methyltetrazol-1-yl)pyridine (1.58 g, 7.0 mmol) in anhydrous DMF (10 mL). The mixture was stirred at 45° C. (bath) for 72 h, before being quenched with a small amount of MeOH and partitioned between EtOAc (75 mL) and saturated aqueous NH$_4$Cl (50 mL). The aqueous layer was extracted further with EtOAc (75 mL). The combined organic extracts were filtered, before being washed with H$_2$O (50 mL) and brine (50 mL). After drying (MgSO$_4$), the solution was filtered and concentrated to give a residue that was purified by flash chromatography (CH$_2$Cl$_2$—THF, 1:0 to 16:1) to provide (E)-methyl 3-cyclopentyl-2-[6-(5-methyltetrazol-1-yl)pyridin-3-yl]acrylate: m/z (ES$^+$)=314.1 [M+H]$^+$. Step 3: This ester (271 mg, 865 μmol) was saponified, using the procedure exemplified by Step 2 of Preparation 3, to furnish the title compound: m/z (ES$^+$)=300.1 [M+H]$^+$.

mL) was treated with sufficient H$_2$O to effect dissolution. n-PrSH (1.96 mL, 21.7 mmol) was added, then the reaction was stirred at 20° C. for 4 h. The mixture was poured onto crushed ice (200 g) and then extracted with CH$_2$Cl$_2$ (2×100 mL). The combined CH$_2$Cl$_2$ extracts were washed with H$_2$O (3×100 mL) and brine (3×100 mL), before being dried (MgSO$_4$). Filtration, solvent evaporation, and column chromatography (IH) provided 5-bromo-3-chloro-2-propylsulfanylpyridine: m/z (ES$^+$)=268.0 [M+H]$^+$. Step 2: Reaction of this bromopyridine (2.73 g, 10.2 mmol) with (Z)-methyl 3-cyclopentyl-2-iodoacrylate (1.84 g, 6.6 mmol), according to the cross-coupling conditions described in Step 2 of Preparation 9, gave (E)-methyl 2-(5-chloro-6-propylsulfanylpyridin-3-yl)-3-cyclopentylacrylate: m/z (ES$^+$)=340.1 [M+H]$^+$. Step 3: Saponification of this ester (770 mg, 2.3 mmol), using a similar protocol to that described by Step 2 of Preparation 3, furnished the title compound: δ$_H$ (CDCl$_3$): 1.05 (t, 3H), 1.40-1.85 (m, 10H), 2.45-2.60 (m, 1H), 3.20 (t, 2H), 7.15 (d, 1H), 7.40 (d, 1H), 8.15 (d, 1H).

The compounds listed in TABLE 2 were made using the procedures described in Preparation 10.

TABLE 2

| Prep | Structure | Name | δ$_H$ (CDCl$_3$): | m/z (ES$^+$) |
|---|---|---|---|---|
| 11 | 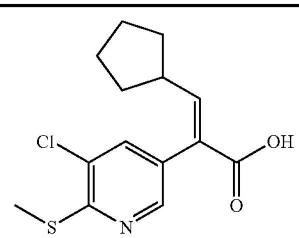 | (E)-2-(5-Chloro-6-methylsulfanylpyridin-3-yl)-3-cyclopentylacrylic acid | 1.40-1.85 (m, 8H), 2.45-2.55 (m, 1H), 2.60 (s, 3H), 7.20 (d, 1H), 7.45 (d, 1H), 8.20 (d, 1H). | — |
| 12 | 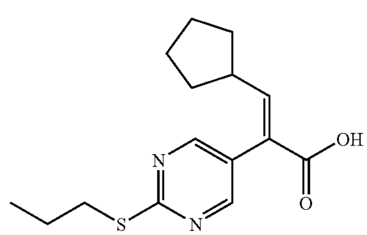 | (E)-3-Cyclopentyl-2-(2-propylsulfanylpyrimidin-5-yl)acrylic acid | — | 293.1 [M + H]$^+$ |

Preparation 10: (E)-2-(5-Chloro-6-propylsulfanylpyridin-3-yl)-3-cyclopentylacrylic Acid

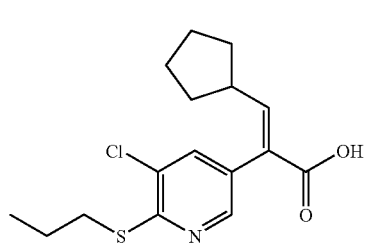

Step 1: A mixture of 5-bromo-2,3-dichloropyridine (4.47 g, 19.7 mmol) and NaOH (867 mg, 21.7 mmol) in DMSO (50

Preparation 13: Triphenyl(tetrahydropyran-4-ylmethyl) phosphonium Iodide

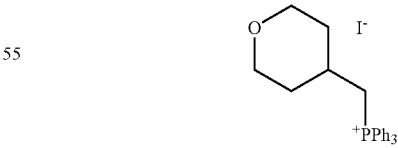

A stirred solution of 4-iodomethyltetrahydropyran (3.43 g, 15.2 mmol) and PPh$_3$ (3.98 g, 15.2 mmol) in anhydrous MeCN (10 mL) was heated under reflux for 19 h. On cooling to 20° C., Et$_2$O (50 mL) was added. The precipitate formed was collected, washed with Et$_2$O (150 mL), and recrystallised (MeCN) to give the title compound: m/z (ES$^+$)=361.2 [M]$^+$.

25

Preparation 14: (E)-3-(Tetrahydropyranyl)-2-(6-methanesulfanylpyridin-3-yl)acrylic Acid

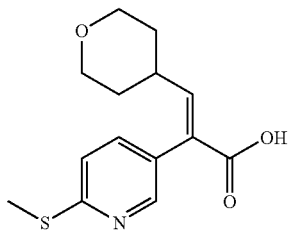

Step 1: n-BuLi (32.9 mL of a 2.6M solution in hexanes, 102 mmol) was added over 15 min to a stirred solution of 2,5-dibromopyridine (23.7 g, 100 mmol) in Et$_2$O (800 mL) at −78° C. After 20 min, diethyl oxalate (16.4 mL, 120 mmol) was added over 15 min, then stirring was continued at −78° C. for 30 min and then at 0° C. for 3 h. The reaction was poured into ice cold saturated aqueous NH$_4$Cl, before being extracted with Et$_2$O. The organic layer was washed with H$_2$O and brine, dried (Na$_2$SO$_4$), filtered, and concentrated in vacuo. Chromatographic purification (EtOAc-n-C$_6$H$_{14}$, 1:6) provided ethyl (6-bromopyridin-3-yl)glyoxylate: m/z (APCI$^+$)=276 [M+H$_2$O+H]$^+$. Step 2: To a solution of this compound (11.6 g, 44.9 mmol) in DMF (200 mL) was added NaSMe (3.15 g, 44.9 mmol) at 0° C. over 5 min. The mixture was stirred at 20° C. for 24 h, before being concentrated in vacuo. The residue was partitioned between EtOAc and H$_2$O. The organic layer was washed with H$_2$O and brine, dried (Na$_2$SO$_4$), filtered, and concentrated. Chromatographic purification (EtOAc-n-C$_6$H$_{14}$, 1:10) yielded ethyl (6-methanesulfanylpyridin-3-yl)glyoxylate: m/z (APCI$^+$)=226 [M+H]$^+$. Step 3: LHMDS (6.25 mL of a 1.0M solution in THF, 6.3 mmol) was added to a stirred suspension of triphenyl(tetrahydropyran-4-ylmethyl)phosphonium iodide (Preparation 13, 3.18 g, 8.5 mmol) in THF (10 mL) at 0° C. After 1 h, a solution of ethyl (6-methylsulfanylpyridin-3-yl)glyoxylate (1.13 g, 5.0 mmol) in THF (4 mL) was added over 5 min. The reaction was stirred at 0° C. for 1 h, before being treated with H$_2$O followed by 10% aqueous HCl to adjust the pH to 6. The mixture was stirred at 20° C. for 1 h, then the THF was removed in vacuo. The remainder was treated with Et$_2$O (50 mL) and filtered. The precipitate collected was washed with Et$_2$O. The filtrate and washings were extracted with Et$_2$O (3×10 mL). The combined organic layers were washed with brine, dried (Na$_2$SO$_4$), filtered, and concentrated. Chromatographic purification of the residue (EtOAc-n-C$_6$H$_{14}$, 1:3) afforded ethyl 3-(4-tetrahydropyranyl)-2-(6-methanesulfanylpyridin-3-yl)acrylate as a 2:1 mixture of (E)- and (Z)-isomers: m/z (APCI$^+$)=308 [M+H]$^+$. Step 4: 2M NaOH (1.5 mL, 3.0 mmol) was added to a solution of this ester (615 mg, 2.0 mmol) in EtOH (3 mL) at 0° C. The mixture was stirred at 20° C. for 24 h, before being concentrated in vacuo. The residue was diluted with H$_2$O (5 mL), acidified with 2M HCl, and extracted with EtOAc. The combined organic layers were washed with brine, dried (Na$_2$SO$_4$), filtered and concentrated in vacuo. Recrystallisation (EtOAc) gave the title compound: m/z (ES$^-$)=278 [M−H]$^-$.

26

Preparation 15: (E)-3-Cyclopentyl-2-(6-cyclopropylsulfanylpyridin-3-yl)acrylic Acid

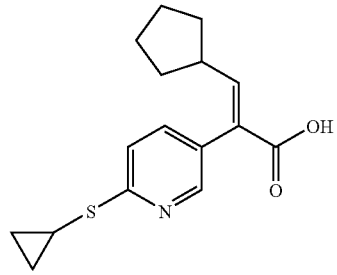

SO$_2$Cl$_2$ (9.8 mL, 122.0 mmol) was added slowly at 0° C. to dicyclopropyldisulfide (17.0 g, 116.2 mmol). The mixture was stirred at 20° C. for 2 h, before being diluted with anhydrous PhMe (100 mL) to give a PhMe solution of cyclopropanesulfenyl chloride. In a separate vessel, n-BuLi (153 mL of a 1.6M solution in hexanes, 244.8 mmol) was added to a stirred solution of 2,5-dibromopyridine (55.1 g, 232.4 mmol) in anhydrous PhMe (1L) at −78° C. After 3 h at −78° C., the abovementioned cyclopropanesulfenyl chloride solution was added slowly to the mixture. After 1 h, the mixture was quenched with saturated aqueous NH$_4$Cl (1L) at −20° C., before being stirred at 20° C. for 16 h. The organic layer was separated, then the aqueous phase was extracted with Et$_2$O (3×500 mL). The organic extracts were combined, dried (MgSO$_4$), filtered, concentrated, and purified by flash column chromatography (IH-Et$_2$O, 98.5:1.5) to furnish 5-bromo-2-cyclopropylsulfanylpyridine: m/z (ES$^+$)=232.0 [M+H]$^+$. Bromine-lithium exchange on this compound (22.0 g, 95.6 mmol) followed by reaction with diethyl oxalate, as described in Step 1 of Preparation 14, gave ethyl (6-cyclopropylsulfanylpyridin-3-yl)oxoacetate: m/z (ES$^+$)=252.2 [M+H]$^+$. Reaction of this oxoester (11.09 g, 44.1 mmol) with cyclopentylmethyltriphenylphosphonium iodide (33.00 g, 75.0 mmol), employing the protocol outlined in Step 3 of Preparation 14, provided ethyl 3-cyclopentyl-2-(6-cyclopropylsulfanylpyridin-3-yl)acrylate as a ca. 2:1 mixture of (E)- and (Z)-isomers: m/z (ES$^+$)=318.2 [M+H]$^+$. Using a similar procedure to that described in Step 4 of Preparation 14, this ester (13.21 g, 41.6 mmol) was hydrolysed to give the title compound: m/z (ES$^+$)=290.3 [M+H]$^+$.

Preparation 16: 3-Cyclopentyl-2-(6-fluoropyridin-3-yl)propionic Acid

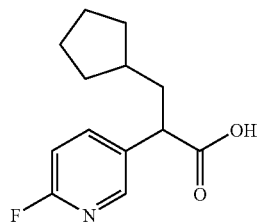

Step 1: Reaction of 5-bromo-2-fluoropyridine (1.50 g, 8.5 mmol) with (Z)-methyl 3-cyclopentyl-2-iodoacrylate (2.60 g, 9.3 mmol), according to the cross-coupling conditions described above in Step 2 of Preparation 9, gave (E)-methyl 3-cyclopentyl-2-(6-fluoropyridin-3-yl)acrylate: m/z (ES$^+$)=250.1 [M+H]$^+$. Step 2: A solution of this α,β-unsaturated ester (1.50 g, 6.0 mmol) in EtOAc was treated with a suspension of Pd (10% on C, 300 mg, 0.3 mmol) in EtOH (0.5 mL). The reaction was stirred under a H₂ atmosphere for 4 d and then filtered through Celite. The solvents were removed under reduced pressure, then the residue was purified by column chromatography to give methyl 3-cyclopentyl-2-(6-fluoropyridin-3-yl)propionate: m/z (ES⁺)=252.2 [M+H]⁺. Step 3: A solution of this ester (1.48 g, 5.9 mmol) and LiOH.H₂O (0.49 g, 11.8 mmol) in THF-H₂O (5:1, 24 mL) was stirred at 20° C. for 18 h. The THF was removed in vacuo, then the remainder was partitioned between saturated aqueous Na₂CO₃ (150 mL) and Et₂O (75 mL). The pH of the aqueous layer was adjusted to 3 with 2M HCl. The remainder was extracted with EtOAc (100 mL+75 mL). The combined organic extracts were washed with brine, dried (MgSO₄), filtered, and concentrated to give the title compound: m/z (ES⁺)=238.1 [M+H]⁺.

(E)-3-Cyclopentyl-2-(6-cyclopropylsulfanylpyridin-3-yl) acrylic acid (Preparation 15, 9.63 g, 33.3 mmol) was oxidised, using the procedure described in EXAMPLE 35, to provide (E)-3-Cyclopentyl-2-(6-cyclopropanesulfonylpyridin-3-yl)propionic acid: δ$_H$ (CDCl₃): 1.05-1.20 (m, 2H), 1.35-1.85 (m, 10H), 2.40-2.50 (m, 1H), 2.80-2.90 (m, 1H), 7.25 (d, 1H), 7.80 (dd, 1H), 8.05 (d, 1H), 8.60 (d, 1H). Reduction of this α,β-unsaturated carboxylic acid, employing a procedure similar to that described in Step 2 of Preparation 16, afforded the title compound: m/z (ES⁺)= 324.2 [M+H]⁺.

The compounds shown in TABLE 3 were prepared by coupling the appropriate carboxylic acid with a thiazol-2-ylamine employing the protocol described in EXAMPLE 5.

TABLE 3

| Prep | Structure | Name | m/z (ES⁺) |
|---|---|---|---|
| 18 | 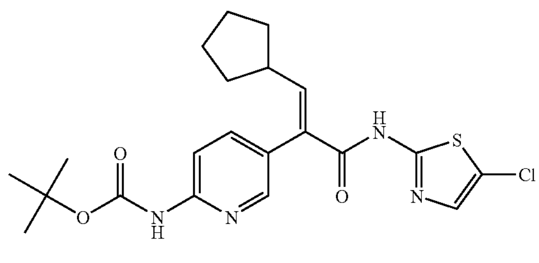 | (E)-tert-Butyl {5-[1-(5-chlorothiazol-2-ylcarbamoyl)-2-cyclopentylvinyl]pyridin-2-yl}carbamate | 449.3 [M + H]⁺ |
| 19 | 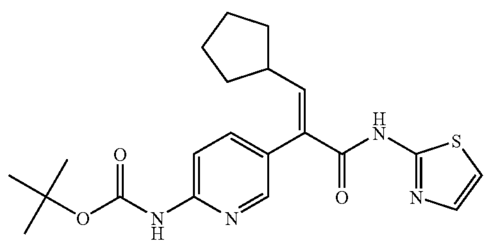 | (E)-tert-Butyl 5-[2-cyclopentyl-1-(thiazol-2-ylcarbamoyl)-vinyl]pyridin-2-yl}carbamate | 415.2 [M + H]⁺ |
| 20 | 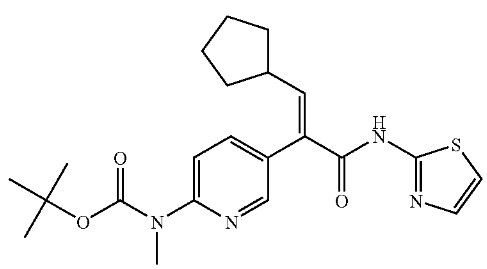 | (E)-tert-Butyl {5-[2-cyclopentyl-1-(thiazol-2-ylcarbamoyl)vinyl]-pyridin-2-yl}methylcarbamate | 429.1 [M + H]⁺ |

Preparation 17: 3-Cyclopentyl-2-(6-cyclopropanesulfonylpyridin-3-yl)propionic Acid

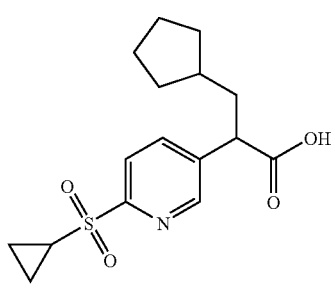

Preparation 21: 5-Fluorothiazol-2-ylamine Hydrochloride

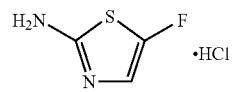

NEt₃ (63.4 mL, 455 mmol) was added to a stirred suspension of 5-bromothiazol-2-ylamine hydrobromide (102.7 g, 379 mmol) in CH₂Cl₂ (1.5L). After 1 h, TFAA (64.2 mL, 455 mmol) was added dropwise at 0° C. over 15 min. The mixture was allowed to warm to 20° C. over 1 h, before being stirred for an additional 2 h. H₂O (600 mL) was added and the resulting precipitate was collected. The aqueous layer of the filtrate was separated and extracted with CHCl₃ (3×300 mL). The combined organic extracts were washed with brine, dried (Na₂SO₄), filtered and concentrated. The collected precipitate and residual solid were combined and triturated with EtOAc-n-C$_6$H$_{14}$ to give N-(5-bromothiazol-2-yl)-2,2,2-trifluoroacetamide: δ$_H$ (CDCl$_3$): 7.45 (s, 1H), 13.05 (br, 1H). n-BuLi (253 mL of a 1.58M solution in hexanes, 403 mmol) was added dropwise over 50 min to a stirred solution of the above amide (50.0 g, 183 mmol) in anhydrous THF (1.3L) at −78° C. After 1.5 h, a solution of N-fluorobenzenesulfonimide (86.0 g, 275 mmol) in anhydrous THF (250 mL) was added dropwise over 30 min. The mixture was stirred for 3 h, before being warmed up to −30° C. H$_2$O (300 mL) was added and the mixture was filtered through a Celite pad. The solid collected and Celite were washed with Et$_2$O (400 mL) and H$_2$O (400 mL). The organic layer of the filtrate was separated and extracted with water (2×400 mL). The combined aqueous layers were washed with Et$_2$O (400 mL), before being acidified to pH 6.5 with 2M HCl and extracted with EtOAc (2×400 mL). The combined organic extracts were washed with H$_2$O (2×400 mL) and brine, before being dried (MgSO$_4$), filtered and concentrated. Column chromatography (EtOAc-n-C$_6$H$_{14}$, 1:3 to 1:2) gave N-(5-fluorothiazol-2-yl)-2,2,2-trifluoroacetamide: δ$_H$ (CDCl$_3$): 7.13 (d, 1H). AcCl (12.6 mL, 175 mmol) was added dropwise to a stirred solution of this amide (15.7 g, 73 mmol) in MeOH (300 mL) at 0° C. The mixture was stirred at 20° C. for 30 min, heated under reflux for 1 h, and finally concentrated in vacuo. The residual solid was triturated with THF to give the title compound: δ$_H$ (D$_2$O): 7.00 (d, 1H).

EXAMPLE 1

2-(6-Chloropyridin-3-yl)-3-cyclopentyl-N-thiazol-2-ylpropionamide

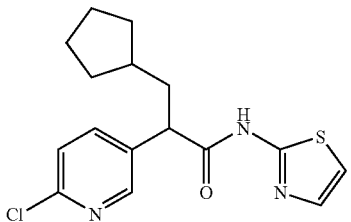

A solution of 2-(6-chloropyridin-3-yl)-3-cyclopentylpropionic acid (Preparation 1, 0.56 g, 2.2 mmol), TBTU (1.41 g, 4.4 mmol), HOBt (0.45 g, 3.3 mmol), NEt$_3$ (0.31 mL, 2.2 mmol), and thiazol-2-ylamine (0.44 g, 4.4 mmol) in anhydrous DMF (23 mL) was stirred at 20° C. for 16 h. The reaction mixture was diluted with EtOAc, before being washed with 2 M Na$_2$CO$_3$, H$_2$O, and brine. After drying (Na$_2$SO$_4$), the organic phase was filtered and concentrated to give the title compound: RT$^4$=3.82 min; m/z (ES$^+$)=336.1 [M+H]$^+$.

EXAMPLE 2

3-Cyclopentyl-2-(6-phenylpyridin-3-yl)-N-thiazol-2-ylpropionamide

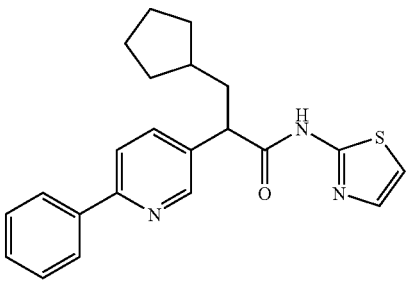

A mixture of 2-(6-chloropyridin-3-yl)-3-cyclopentyl-N-thiazol-2-ylpropionamide (EXAMPLE 1, 100 mg, 297 μmol), Pd(PPh$_3$)$_4$ (5 mg, 4 μmol), (R)-(+)-BINAP (5 mg, 8 μmol), K$_2$CO$_3$ (100 mg, 724 μmol), and benzeneboronic acid (100 mg, 820 μmol) in DMF (1 mL) was heated at 150° C. for 48 h with stirring. The cooled reaction mixture was diluted with EtOAc (50 mL), before being washed with H$_2$O (3×20 mL). The solvent was removed under reduced pressure, then the residue was purified by RP-HPLC to give the title compound: RT$^4$=3.93 min; m/z (ES$^+$)=378.2 [M+H]$^+$.

EXAMPLE 3

3-Cyclopentyl-N-thiazol-2-yl-2-(6-thiophen-3-ylpyridin-3-yl)propionamide

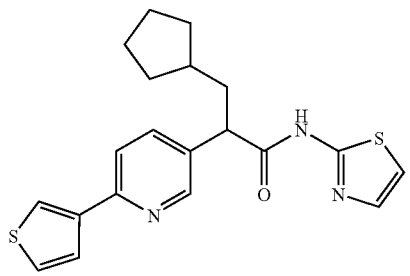

Cross-coupling of 2-(6-chloropyridin-3-yl)-3-cyclopentyl-N-thiazol-2-ylpropionamide (EXAMPLE 1, 100 mg, 297 μmol) with thiophene-3-boronic acid (100 mg, 781 μmol), utilising a procedure similar to that described above for EXAMPLE 2, furnished the title compound: RT$^4$=3.83 min; m/z (ES$^+$)=384.2 [M+H]$^+$.

EXAMPLE 4

3-Cyclopentyl-2-pyridin-3-yl-N-thiazol-2-ylpropionamide

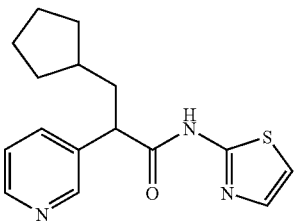

Employing the protocol described in EXAMPLE 1, 3-cyclopentyl-2-pyridin-3-ylpropionic acid (Preparation 2, 0.96 g, 4.4 mmol) was condensed with thiazol-2-ylamine (0.88 g, 8.8 mmol) to give the title compound: RT$^4$=3.05 min; m/z (ES$^+$)=302.0 [M+H]$^+$.

EXAMPLE 5

(E)-3-Cyclopentyl-2-(6-methylsulfanylpyridin-3-yl)-N-thiazol-2-ylacrylamide

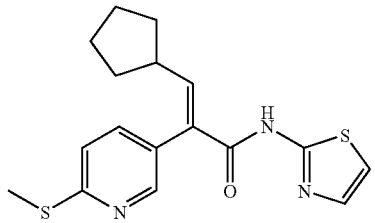

A suspension of PS-carbodiimide (1.08 g, loading 1.32 mmol g$^{-1}$, 1.42 mmol), (E)-3-cyclopentyl-2-(6-methylsulfanylpyridin-3-yl)acrylic acid (Preparation 3, 125 mg, 475 μmol), and HOBt (128 mg, 949 μmol) in anhydrous DMF (8 mL) was stirred for 15 min at 20° C. Thiazol-2-ylamine (48 mg, 475 μmol) was added, then the mixture was stirred for 14 h at 20° C. LCMS indicated that the reaction had not gone to completion, so more thiazol-2-ylamine (95 mg, 950 μmol) was added. The mixture was stirred for an additional 64 h, before being filtered. The resin collected was washed with CH$_2$Cl$_2$, then the combined filtrate and washings were concentrated under reduced pressure. Column chromatography (2:11H-EtOAc) provided the title compound: RT$^4$=3.85 min; m/z (ES$^+$)=346.1 [M+H]$^+$.

The procedure described in EXAMPLE 5 was utilised to prepare the compounds listed in TABLE 4.

TABLE 4

| Ex | Structure | Name | RT (min) | m/z (ES$^+$) |
|---|---|---|---|---|
| 6 | 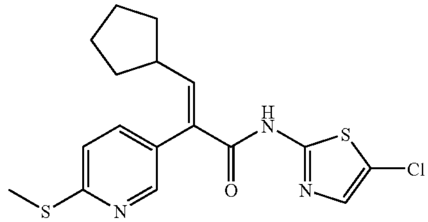 | (E)-N-(5-Chlorothiazol-2-yl)-3-cyclopentyl-2-(6-methylsulfanylpyridin-3-yl)acrylamide | 4.23[A] | 380.1 [M + H]$^+$ |
| 7 | 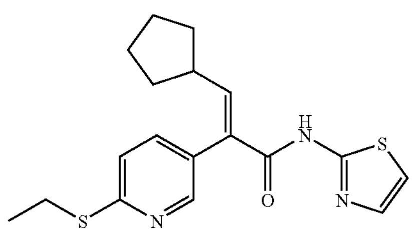 | (E)-3-Cyclopentyl-2-(6-ethylsulfanylpyridin-3-yl)-N-thiazol-2-ylacrylamide | 4.11[A] | 360.2 [M + H]$^+$ |
| 8 | 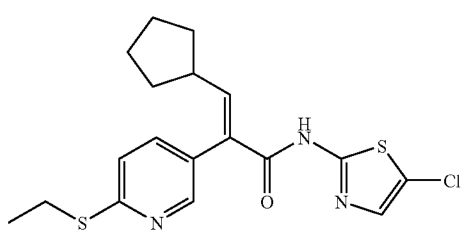 | (E)-N-(5-Chlorothiazol-2-yl)-3-cyclopentyl-2-(6-ethylsulfanylpyridin-3-yl)acrylamide | 4.40[A] | 394.2 [M + H]$^+$ |
| 9 | 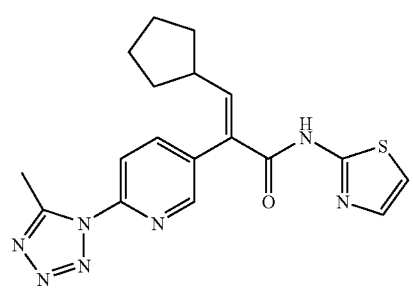 | (E)-3-Cyclopentyl-2-[6-(5-methyltetrazol-1-yl)pyridin-3-yl]-N-thiazol-2-ylacrylamide | 1.60[B] | 382.0 [M + H]$^+$ |

TABLE 4-continued

| Ex | Structure | Name | RT (min) | m/z (ES⁺) |
|---|---|---|---|---|
| 10 | 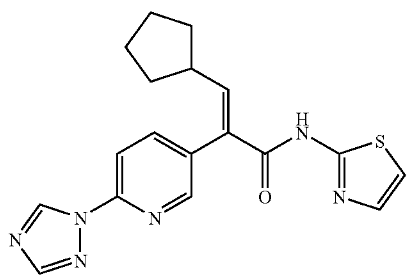 | (E)-3-Cyclopentyl-N-thiazol-2-yl-2-(6-[1,2,4]triazol-1-ylpyridin-3-yl)acrylamide | 3.52[A] | 367.1 [M + H]⁺ |
| 11 | 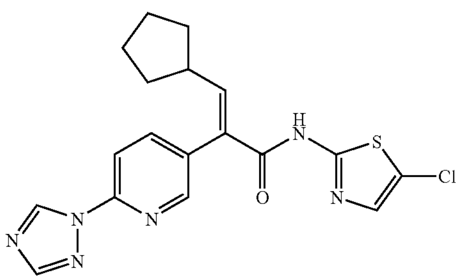 | (E)-N-(5-Chlorothiazol-2-yl)-3-cyclopentyl-2-(6-[1,2,4]triazol-1-ylpyridin-3-yl)acrylamide | 3.93[A] | 401.1 [M + H]⁺ |

[A]RT measured using Method A.
[B]RT measured using Method B.

EXAMPLE 12

(E)-3-Cyclopentyl-2-(5-methylsulfanylpyridin-2-yl)-N-thiazol-2-ylacrylamide

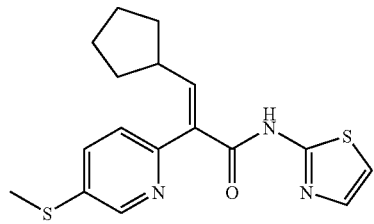

A solution of (E)-3-cyclopentyl-2-(5-methylsulfanylpyridin-2-yl)acrylic acid (Preparation 5, 1.00 g, 3.8 mmol), EDCI (0.95 g, 4.9 mmol), HOBt (0.67 g, 4.9 mmol) and thiazol-2-ylamine (1.52 g, 15.2 mmol) in anhydrous THF (62 mL) and DMF (50 mL) was stirred at 20° C. for 4 d. The solvents were evaporated off under reduced pressure, then the residue was partitioned between $CH_2Cl_2$ and saturated aqueous $Na_2CO_3$. The organic layer was washed with $H_2O$ and brine, before being dried ($MgSO_4$). Filtration, solvent evaporation, and column chromatography (7:31H-EtOAc) provided the title compound: RT⁴=3.96 min; m/z (ES⁺)= 346.1 [M+H]⁺.

The compounds listed in TABLE 5 were synthesised using the method described in EXAMPLE 12.

TABLE 5

| Ex | Structure | Name | RT (min) | m/z (ES⁺) |
|---|---|---|---|---|
| 13 | 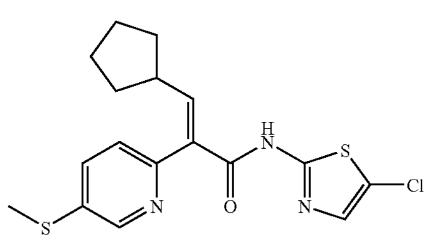 | (E)-N-(5-Chlorothiazol-2-yl)-3-cyclopentyl-2-(5-methylsulfanylpyridin-2-yl)acrylamide | 4.32[A] | 380.0 [M + H]⁺ |

TABLE 5-continued

| Ex | Structure | Name | RT (min) | m/z (ES⁺) |
|---|---|---|---|---|
| 14 | 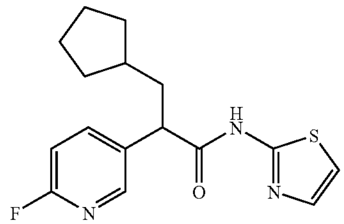 | 3-Cyclopentyl-2-(6-fluoropyridin-3-yl)-N-thiazol-2-ylpropionamide | 1.61[B] | 320.1 [M + H]⁺ |
| 15 | 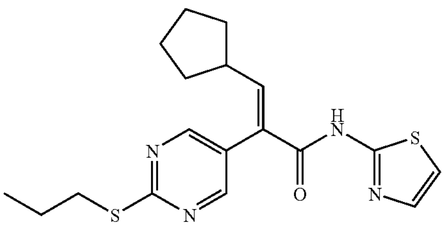 | (E)-3-Cyclopentyl-2-(2-propylsulfanylpyrimidin-5-yl)-N-thiazol-2-ylacrylamide | 1.93[B] | 375.0 [M + H]⁺ |

[A]RT measured using Method A.
[B]RT measured using Method B.

EXAMPLE 16

(E)-3-(4-Tetrahydropyranyl)-2-(6-methanesulfanylpyridin-3-yl)-N-thiazol-2-ylacrylamide

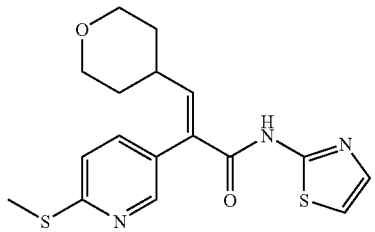

A solution of (E)-3-(4-tetrahydropyranyl)-2-(6-methanesulfanylpyridin-3-yl)acrylic acid (Preparation 14, 280 mg, 1.0 mmol) in THF (4 mL) was added to a suspension of DMF (126 μL, 1.6 mmol) and oxalyl chloride (280 mg, 11.0 mmol) in THF (3 mL) at −25° C. The mixture was stirred at 0° C. for 1 h and then at 20° C. for 1 h. A solution of thiazol-2-ylamine (320 mg, 3.2 mmol) and NEt₃ (446 μL, 3.2 mmol) in THF (2 mL) was added at −45° C. over 10 min, then the mixture was stirred at 0° C. for 1 h. Saturated aqueous NaHCO₃ was added and the mixture was filtered through Celite. The aqueous layer of the filtrate was extracted with EtOAc. The combined organic layers were washed with brine, dried (Na₂SO₄), filtered, and concentrated in vacuo. Column chromatographic purification (EtOAc-n-C₆H₁₄, 1:3 to 1:1, then CHCl₃—MeOH, 99:1) gave the title compound: $\delta_H$ (CDCl₃): 1.46-1.56 (m, 4H), 2.22-2.40 (m, 1H), 2.54 (s, 3H), 3.17-3.29 (m, 2H), 3.80 (dt, 2H), 6.78 (d, 1H), 7.22 (d, 1H), 7.34 (dd, 1H), 7.50 (d, 1H), 7.52 (dd, 1H), 8.27 (dd, 1H), 12.19 (s, 1H); m/z (APCI⁺)= 362 [M+H]⁺.

Procedures similar to those described in EXAMPLE 16 were employed to synthesise the compounds listed in TABLE 6.

TABLE 6

| Ex | Structure | Name | RT^A (min) | m/z (ES⁺) |
|---|---|---|---|---|
| 17 | 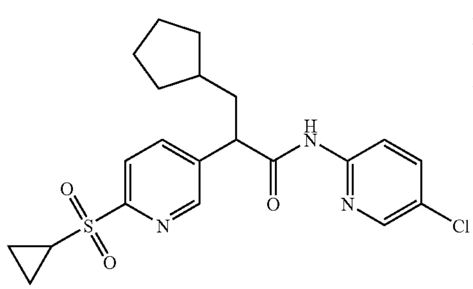 | N-(5-Chloropyridin-2-yl)-3-cyclopentyl-2-(6-cyclopropanesulfonyl-yl)propionamide | 3.94 | 434.3 [M + H]⁺ |

TABLE 6-continued

| Ex | Structure | Name | RT[A] (min) | m/z (ES+) |
|---|---|---|---|---|
| 18 | 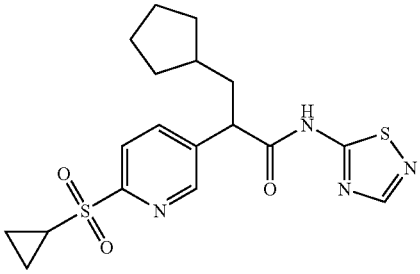 | 3-Cyclopentyl-2-(6-cyclopropanesulfonyl-pyridin-3-yl)-N-[1,2,4]thiadiazol-5-yl-propionamide | 3.57 | 407.3 [M + H]+ |
| 19 | 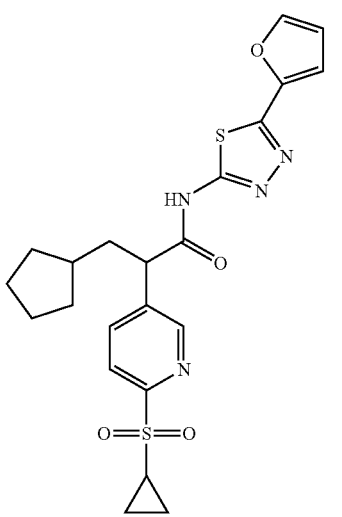 | 3-Cyclopentyl-2-(6-cyclopropanesulfonyl-pyridin-3-yl)-N-(5-furan-2-yl-[1,3,4]thiadiazol-2-yl)propionamide | 3.97 | 473.3 [M + H]+ |
| 20 | 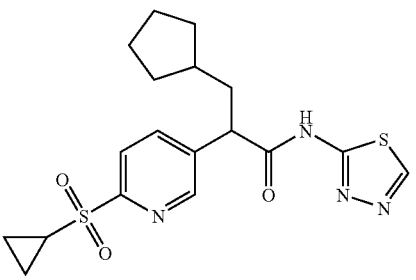 | 3-Cyclopentyl-2-(6-cyclopropanesulfonyl-pyridin-3-yl)-N-[1,3,4]thiadiazol-2-ylpropionamide | 3.37 | 407.3 [M + H]+ |
| 21 | 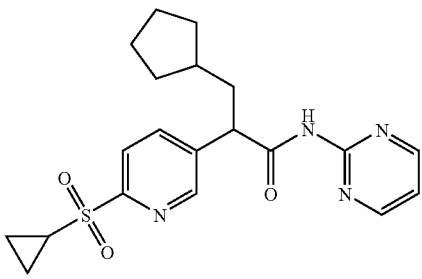 | 3-Cyclopentyl-2-(6-cyclopropanesulfonyl-pyridin-3-yl)-N-pyrimidin-2-ylpropionamide | 3.20 | 401.3 [M + H]+ |

TABLE 6-continued

| Ex | Structure | Name | RT^A (min) | m/z (ES+) |
|---|---|---|---|---|
| 22 | 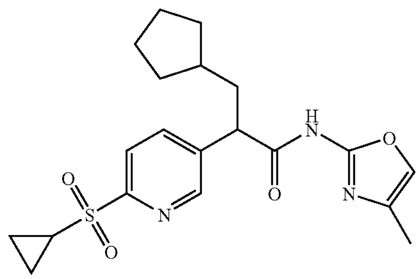 | 3-Cyclopentyl-2-(6-cyclopropanesulfonyl-pyridin-3-yl)-N-(4-methyloxazol-2-yl)propionamide | 3.36 | 404.3 [M + H]+ |
| 23 | 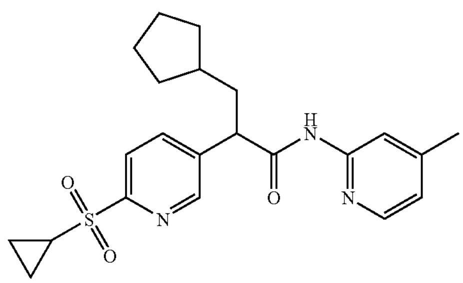 | 3-Cyclopentyl-2-(6-cyclopropanesulfonyl-pyridin-3-yl)-N-(4-methylpyridin-2-yl)propionamide | 3.87 | 414.3 [M + H]+ |
| 24 | 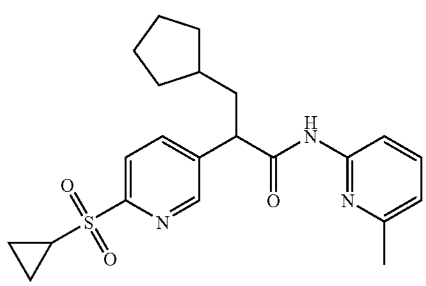 | 3-Cyclopentyl-2-(6-cyclopropanesulfonyl-pyridin-3-yl)-N-(6-methylpyridin-2-yl)propionamide | 3.37 | 414.3 [M + H]+ |
| 25 | 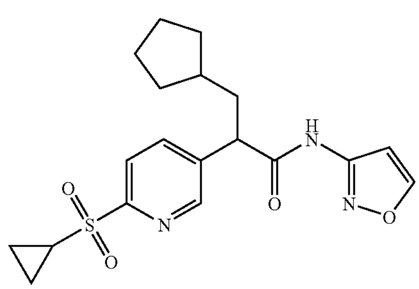 | 3-Cyclopentyl-2-(6-cyclopropanesulfonyl-pyridin-3-yl)-N-isoxazol-3-ylpropionamide | 3.57 | 390.3 [M + H]+ |
| 26 | 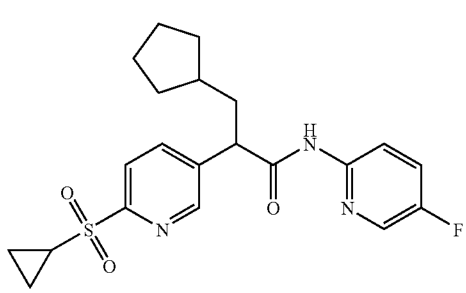 | 3-Cyclopentyl-2-(6-cyclopropanesulfonyl-pyridin-3-yl)-N-(5-fluoropyridin-2-yl)propionamide | 3.82 | 418.3 [M + H]+ |

TABLE 6-continued

| Ex | Structure | Name | RT^A (min) | m/z (ES+) |
|----|-----------|------|------------|-----------|
| 27 | 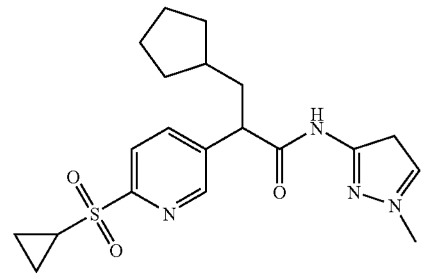 | 3-Cyclopentyl-2-(6-cyclopropanesulfonyl-pyridin-3-yl)-N-(1-methyl-1H-pyrazol-3-yl)propionamide | 3.36 | 403.3 [M + H]+ |
| 28 | 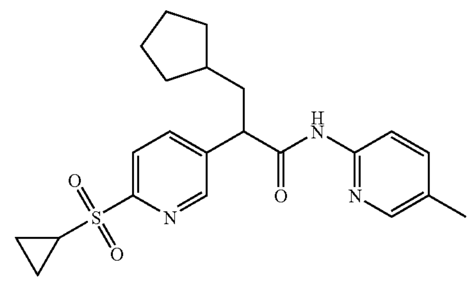 | 3-Cyclopentyl-2-(6-cyclopropanesulfonyl-pyridin-3-yl)-N-(5-methylpyridin-2-yl)propionamide | 3.61 | 414.3 [M + H]+ |
| 29 | 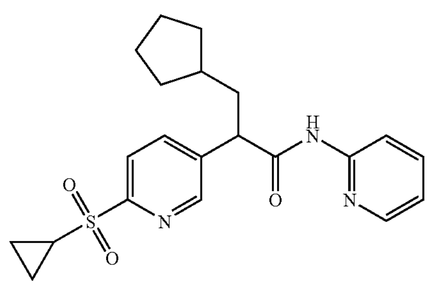 | 3-Cyclopentyl-2-(6-cyclopropanesulfonyl-pyridin-3-yl)-N-pyridin-2-ylpropionamide | 3.72 | 400.3 [M + H]+ |
| 30 | 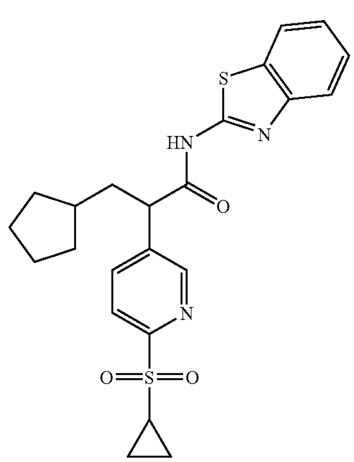 | N-Benzothiazol-2-yl-3-cyclopentyl-2-(6-cyclopropanesulfonyl-pyridin-3-yl)propionamide | 4.02 | 456.3 [M + H]+ |

TABLE 6-continued

| Ex | Structure | Name | RT^A (min) | m/z (ES+) |
|---|---|---|---|---|
| 31 | 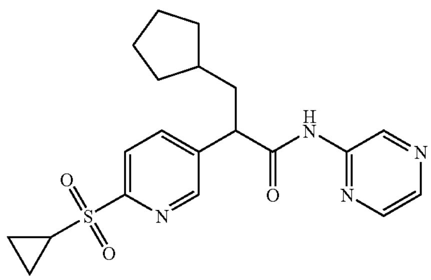 | 3-Cyclopentyl-2-(6-cyclopropanesulfonyl-pyridin-3-yl)-N-pyrazin-2-ylpropionamide | 3.42 | 401.3 [M + H]+ |
| 32 | 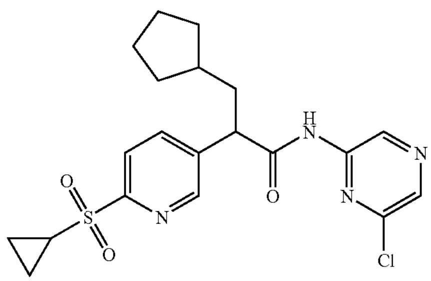 | N-(6-Chloropyrazin-2-yl)-3-cyclopentyl-2-(6-cyclopropanesulfonyl-pyridin-3-yl)propionamide | 3.84 | 435.3 [M + H]+ |
| 33 | 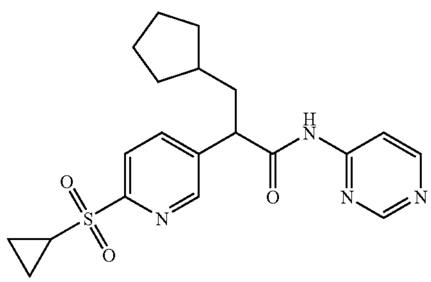 | 3-Cyclopentyl-2-(6-cyclopropanesulfonyl-pyridin-3-yl)-N-pyrimidin-4-ylpropionamide | 3.40 | 401.3 [M + H]+ |
| 34 | 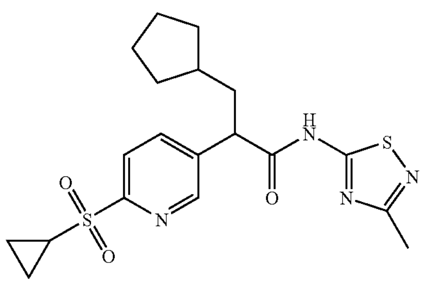 | 3-Cyclopentyl-2-(6-cyclopropanesulfonyl-pyridin-3-yl)-N-(3-[1,2,4]thiadiazol-5-yl)propionamide | 3.77 | 421.2 [M + H]+ |

EXAMPLE 35

(E)-3-Cyclopentyl-2-(6-methanesulfonylpyridin-3-yl)-N-thiazol-2-ylacrylamide

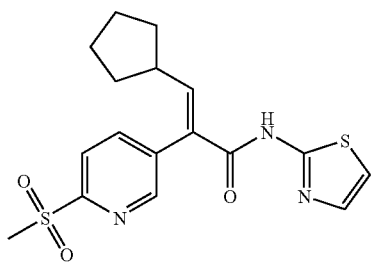

mCPBA (65% pure, 60 mg, 226 μmol) was added to a stirred solution of (E)-3-cyclopentyl-2-(6-methylsulfanylpyridin-3-yl)-N-thiazol-2-ylacrylamide (EXAMPLE 5, 39 mg, 113 μmol) in CH$_2$Cl$_2$ (3 mL). After 16 h, the reaction mixture was concentrated under reduced pressure. EtOAc (15 mL) and saturated aqueous NaHCO$_3$ (5 mL) were added, then the mixture was stirred vigourously for 20 min. The organic layer was separated, before being washed with brine (5 mL) and dried (MgSO$_4$). Filtration, solvent evaporation, and column chromatography (1:1 IH-EtOAc) afforded the title compound: RT$^A$=3.49 min; m/z (ES+)=419.2 [M+MeCN+H]+.

The procedure described in EXAMPLE 35 was utilised to synthesise the compounds listed in TABLE 7.

TABLE 7

| Ex | Structure | Name | RT$^A$ (min) | m/z (ES$^+$) |
|---|---|---|---|---|
| 36 | 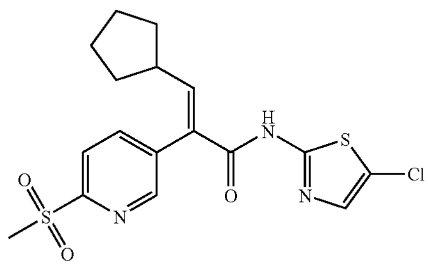 | (E)-N-(5-Chlorothiazol-2-yl)-3-cyclopentyl-2-(6-methanesulfonyl-pyridin-3-yl)acrylamide | 3.85 | 453.2 [M + MeCN + H]$^+$ |
| 37 | 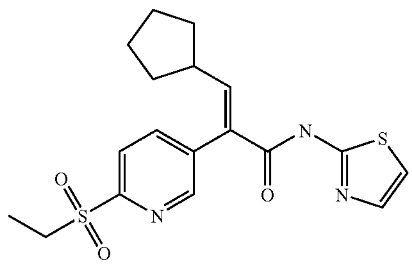 | (E)-3-Cyclopentyl-2-(6-ethanesulfonylpyridin-3-yl)-N-thiazol-2-ylacrylamide | 3.63 | 433.2 [M + MeCN + H]$^+$ |
| 38 | 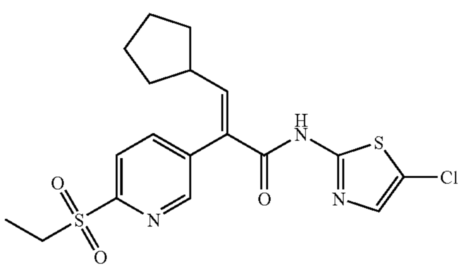 | (E)-N-(5-Chlorothiazol-2-yl)-3-cyclopentyl-2-(6-ethanesulfonyl-pyridin-3-yl)acrylamide | 3.95 | 467.2 [M + MeCN + H]$^+$ |
| 39 | 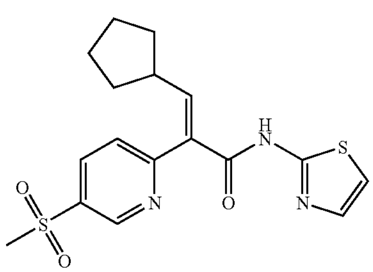 | (E)-3-Cyclopentyl-2-(5-methanesulfonyl-pyridin-2-yl)-N-thiazol-2-ylacrylamide | 3.57 | 378.1 [M + H]$^+$ |

EXAMPLE 40

(E)-N-(5-Bromothiazol-2-yl)-3-cyclopentyl-2-(6-methanesulfonylpyridin-3-yl)acrylamide

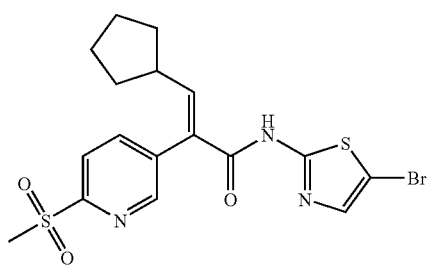

Condensation of (E)-3-cyclopentyl-2-(6-methylsulfanylpyridin-3-yl)acrylic acid (Preparation 3, 64 mg, 0.24 mmol) with 5-bromothiazol-2-ylamine (218 mg, 1.22 mmol), by the protocol described in EXAMPLE 5, yielded (E)-N-(5-bromothiazol-2-yl)-3-cyclopentyl-2-(6-methylsulfanylpyridin-3-yl)acrylamide: RT$^4$=4.28 min; m/z (ES$^+$)= 426.2 [M+H]$^+$. This compound (61 mg, 144 μmol) was oxidised, employing the procedure described in EXAMPLE 35, to give the title compound: RT$^4$=3.91 min; m/z (ES$^+$)= 499.2 [M+MeCN+H]$^+$.

The protocols described in EXAMPLES 12 and 35 were combined for the construction of the compounds listed in TABLE 8.

TABLE 8

| Ex | Structure | Name | RT$^A$ (min) | m/z (ES$^+$) |
|---|---|---|---|---|
| 41 | 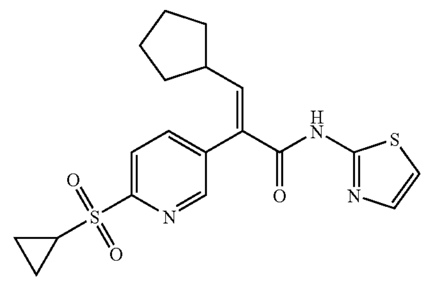 | (E)-3-Cyclopentyl-2-(6-cyclopropanesulfonyl-pyridin-3-yl)-N-thiazol-2-ylacrylamide | 3.49 | 404.3 [M + H]$^+$ |
| 42 | 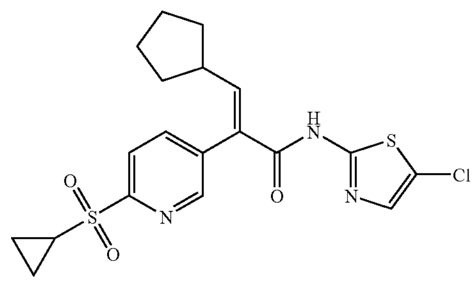 | (E)-N-(5-Chlorothiazol-2-yl)-3-cyclopentyl-2-(6-cyclopropanesulfonyl-pyridin-3-yl)acrylamide | 3.95 | 438.3 [M + H]$^+$ |
| 43 | 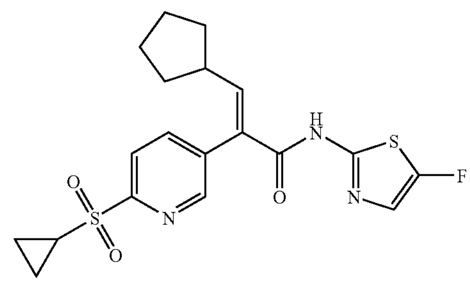 | (E)-3-Cyclopentyl-2-(6-cyclopropanesulfonyl-pyridin-3-yl)-N-(5-fluoro-thiazol-2-yl)acrylamide | 3.73 | 422.2 [M + H]$^+$ |

EXAMPLE 44

(E)-2-[3-Cyclopentyl-2-(6-cyclopropanesulfonylpyridin-3-yl)acryloylamino]thiazole-5-carboxylic Acid Methylamide

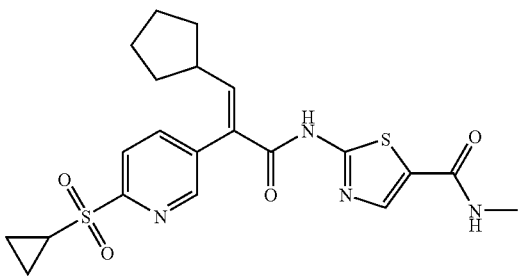

(E)-3-Cyclopentyl-2-(6-cyclopropylsulfanylpyridin-3-yl) acrylic acid (Preparation 15, 250 mg, 0.86 mmol) was condensed with ethyl 2-aminothiazole-5-carboxylate (297 mg, 1.73 mmol), using the method described in EXAMPLE 12, to furnish ethyl 2-[3-cyclopentyl-2-(6-cyclopropylsulfanylpyridin-3-yl)acryloylamino]thiazole-5-carboxylate: m/z (ES$^+$)=444.3 [M+H]$^+$. This ester was saponified, employing a procedure similar to that described in Step 3 of Preparation 16, to give 2-[3-cyclopentyl-2-(6-cyclopropylsulfanylpyridin-3-yl)acryloylamino]thiazole-5-carboxylic acid: m/z (ES$^+$)=416.1 [M+H]$^+$. Oxidation of this thioether, utilising an approach similar to that described in EXAMPLE 35, afforded 2-[3-cyclopentyl-2-(6-cyclopropanesulfonylpyridin-3-yl)acryloylamino]thiazole-5-carboxylic acid: m/z (ES$^+$)=448.2 [M+H]$^+$. This carboxylic acid (52 mg, 116 μmol) was condensed with MeNH$_2$.HCl in the presence of NEt$_3$, utilising the general procedure described in EXAMPLE 12, to give the title compound: RT$^A$=3.29 min; m/z (ES$^+$)=461.3 [M+H]$^+$.

EXAMPLES 45 AND 46

(E)-N-(5-Chlorothiazol-2-yl)-3-cyclopentyl-2-(5-methanesulfonylpyridin-2-yl)acrylamide and (E)-N-(5-Chlorothiazol-2-yl)-3-cyclopentyl-2-(5-methanesulfinylpyridin-2-yl)acrylamide

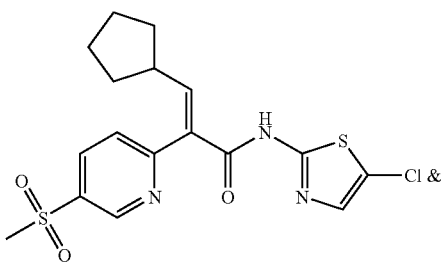

-continued

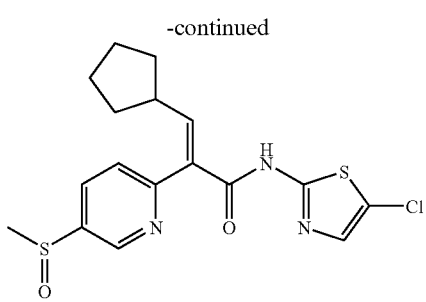

mCPBA (60% pure, 158 mg, 548 µmol) was added to a solution of (E)-N-(5-chlorothiazol-2-yl)-3-cyclopentyl-2-(5-methylsulfanylpyridin-2-yl)acrylamide (EXAMPLE 13, 200 mg, 525 µmol) in $CH_2Cl_2$ (10 mL). The mixture was stirred at 20° C. for 16 h, then more mCPBA (60% pure, 53 mg, 184 µmol) was added. After 30 min, the reaction was quenched with saturated aqueous $Na_2CO_3$. The organic layer was washed with saturated aqueous $NaHCO_3$, before being dried ($MgSO_4$), filtered, concentrated, and purified by column chromatography. The title sulfone was obtained by eluting the column with 3:21H-EtOAc: $RT^A$=3.90 min; m/z ($ES^+$)=412.0 $[M+H]^+$. The title sulfoxide was obtained when the column was eluted with 1:9 MeOH-EtOAc: Further purification was achieved by diffusing IH vapour into an EtOAc solution of this compound. $RT^A$=3.73 min; m/z ($ES^+$)=396.0 $[M+H]^+$.

Protocols similar to that described for EXAMPLE 5 were combined with the one used to prepare EXAMPLES 45 and 46 for the synthesis of the compounds listed in TABLE 9.

TABLE 9

| Ex | Structure | Name | $RT^A$ (min) | m/z ($ES^+$) |
|---|---|---|---|---|
| 47 | 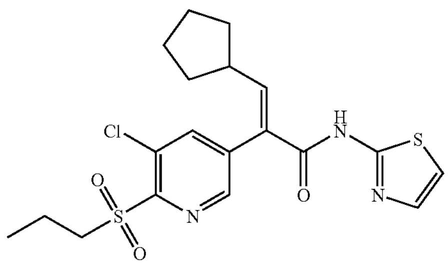 | (E)-2-[5-Chloro-6-(propane-1-sulfonyl)-pyridin-3-yl]-3-cyclopentyl-N-thiazol-2-ylacrylamide | 3.93 | 481.2 $[M + MeCN + H]^+$ |
| 48 | 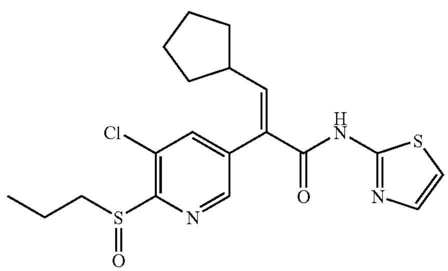 | (E)-2-[5-Chloro-6-(propane-1-sulfinyl)pyridin-3-yl]-3-cyclopentyl-N-thiazol-2-ylacrylamide | 3.73 | 424.1 $[M + H]^+$ |
| 49 | 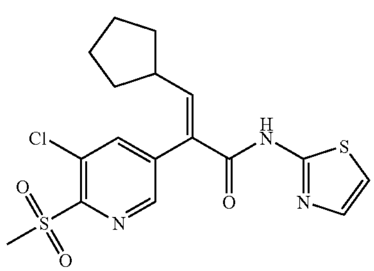 | (E)-2-(5-Chloro-6-methanesulfonylpyridin-3-yl)-3-cyclopentyl-N-thiazol-2-ylacrylamide | 3.65 | 453.1 $[M + MeCN + H]^+$ |
| 50 | 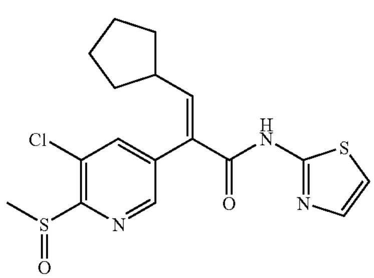 | (E)-2-(5-Chloro-6-methanesulfinylpyridin-3-yl)-3-cyclopentyl-N-thiazol-2-ylacrylamide | 3.38 | 396.1 $[M + H]^+$ |

TABLE 9-continued

| Ex | Structure | Name | RT^A (min) | m/z (ES+) |
|---|---|---|---|---|
| 51 | 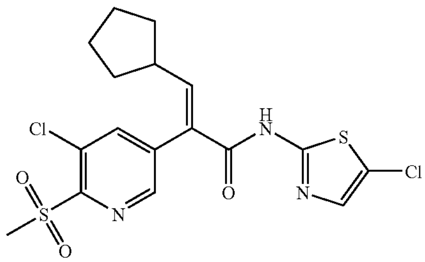 | (E)-2-(5-Chloro-6-methane-sulfonylpyridin-3-yl)-N-(5-chlorothiazol-2-yl)-3-cyclopentylacrylamide | 3.93 | 487.1 [M + MeCN + H]+ |
| 52 | 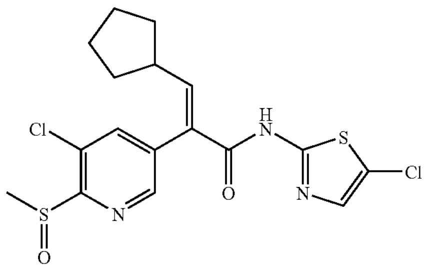 | (E)-2-(5-Chloro-6-methane-sulfinylpyridin-3-yl)-N-(5-chlorothiazol-2-yl)-3-cyclopentylacrylamide | 3.73 | 430.1 [M + H]+ |
| 53 | 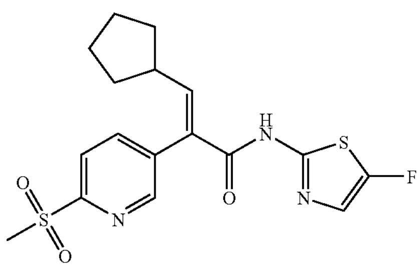 | (E)-3-Cyclopentyl-N-(5-fluorothiazol-2-yl)-2-(6-methanesulfonyl-pyridin-3-yl)acrylamide | 3.65 | 396.2 [M + H]+ |
| 54 | 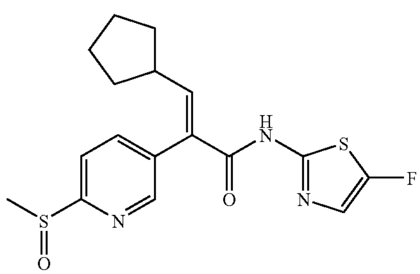 | (E)-3-Cyclopentyl-N-(5-fluorothiazol-2-yl)-2-(6-methanesulfinyl-pyridin-3-yl)acrylamide | 3.44 | 380.2 [M + H]+ |

EXAMPLE 55

(E)-3-Cyclopentyl-2-(6-methanesulfinylpyridin-3-yl)-N-thiazol-2-ylacrylamide

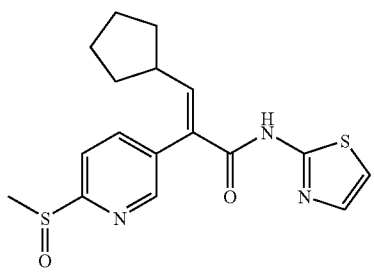

A solution of mCPBA (85% pure, 64 mg, 318 μmol) in CH$_2$Cl$_2$ (1 mL) was added over 5 min to a stirred solution of (E)-3-cyclopentyl-2-(6-methylsulfanylpyridin-3-yl)-N-thiazol-2-ylacrylamide (EXAMPLE 5, 110 mg, 318 μmol) in CH$_2$Cl$_2$ (5 mL) at 0° C. After 4.5 h at 0° C., the reaction mixture was diluted with EtOAc (40 mL). The resulting solution was washed with H$_2$O-saturated aqueous NaHCO$_3$ (1:1, 2×20 mL) and brine (20 mL), before being dried (MgSO$_4$). Filtration, solvent evaporation, and column chromatography (EtOAc then THF) provided the title compound: RT$^A$=3.32 min; m/z (ES+)=362.1 [M+H]+.

TABLE 10 lists the compounds which were made utilising the protocol described in EXAMPLE 55.

TABLE 10

| Ex | Structure | Name | RT$^A$ (min) | m/z (ES$^+$) |
|---|---|---|---|---|
| 56 | 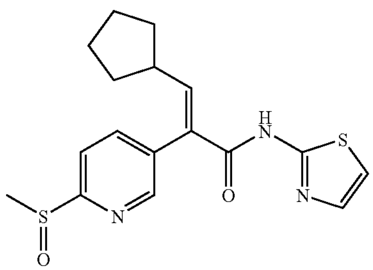 | (E)-3-Cyclopentyl-2-(6-ethanesulfinylpyridin-3-yl)-N-thiazol-2-ylacrylamide | 3.52 | 376.1 [M + H]$^+$ |
| 57 | 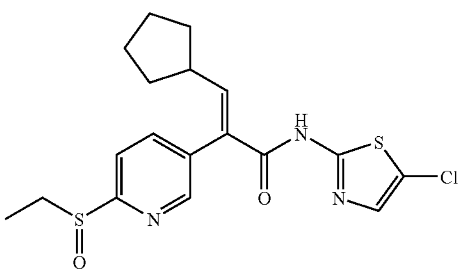 | (E)-N-(5-Chlorothiazol-2-yl)-3-cyclopentyl-2-(6-ethanesulfinyl-pyridin-3-yl)acrylamide | 3.83 | 410.1 [M + H]$^+$ |
| 58 | 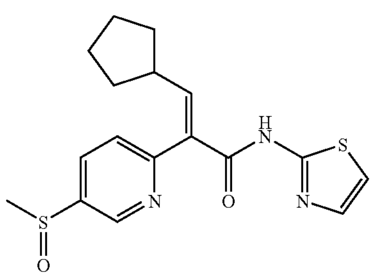 | (E)-3-Cyclopentyl-2-(5-methanesulfinylpyridin-2-yl)-N-thiazol-2-ylacrylamide | 3.30 | 362.1 [M + H]$^+$ |
| 59 | 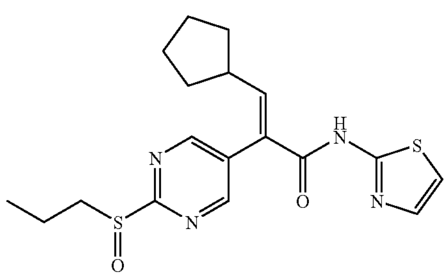 | (E)-3-Cyclopentyl-2-[2-(propane-1-sulfinyl)-pyrimidin-5-yl]-N-thiazol-2-ylacrylamide | 3.40 | 391.2 [M + H]$^+$ |

EXAMPLE 60

(E)-3-Cyclopentyl-2-(6-ethanesulfinylpyridin-3-yl)-N-(5-fluorothiazol-2-yl)acrylamide

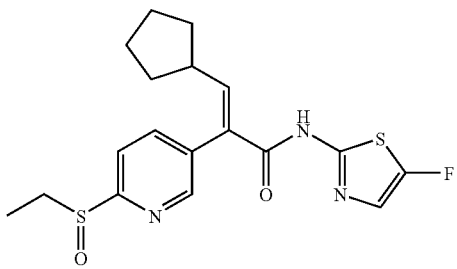

Condensation of (E)-3-cyclopentyl-2-(6-ethylsulfanylpyridin-3-yl)acrylic acid (Preparation 4, 215 mg, 0.78 mmol) with 5-fluorothiazol-2-ylamine hydrochloride (Preparation 21, 240 mg, 1.55 mmol), by the protocol described in EXAMPLE 5, yielded (E)-3-cyclopentyl-2-(6-ethylsulfanylpyridin-3-yl)-N-(5-fluorothiazol-2-yl)acrylamide: m/z (ES$^+$)=378.2 [M+H]$^+$. Oxidation of this thioether (22 mg, 60 µmol), by the protocol described in EXAMPLE 55, gave the title compound: RT$^A$=3.50 min; m/z (ES$^+$)=394.2 [M+H]$^+$.

Protocols similar to those described in EXAMPLE 60 were employed for the synthesis of the compounds listed in TABLE 11.

TABLE 11

| Ex | Structure | Name | RT^A (min) | m/z (ES+) |
|---|---|---|---|---|
| 61 | 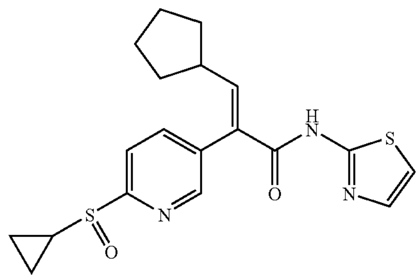 | (E)-3-Cyclopentyl-2-(6-cyclopropanesulfinyl-pyridin-3-yl)-N-thiazol-2-ylacrylamide | 3.26 | 388.2 [M + H]+ |
| 62 | 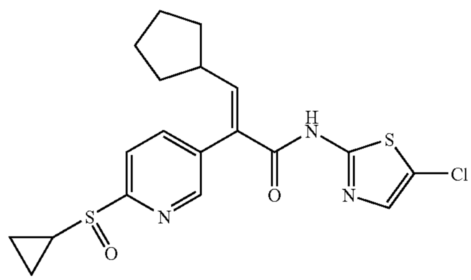 | (E)-N-(5-Chlorothiazol-2-yl)-3-cyclopentyl-2-(6-cyclopropanesulfinyl-pyridin-3-yl)acrylamide | 3.76 | 422.2 [M + H]+ |
| 63 | 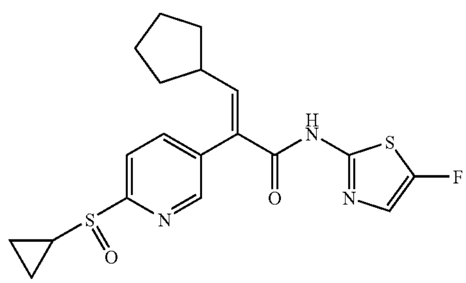 | (E)-3-Cyclopentyl-2-(6-cyclopropanesulfinyl-pyridin-3-yl)-N-(5-fluoro-thiazol-2-yl)acrylamide | 3.56 | 423.2 [M + NH4]+ |

EXAMPLE 64

(E)-3-Cyclopentyl-2-(6-methanesulfinylpyridin-3-yl)-N-(5-chlorothiazol-2-yl)acrylamide

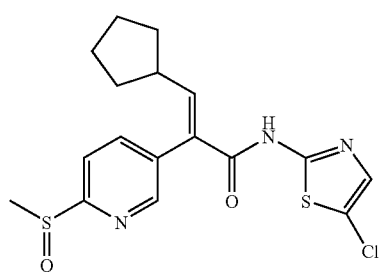

A solution of oxone® (190 mg, 0.98 mmol) in H₂O (2 mL) was added to a stirred solution of (E)-3-cyclopentyl-2-(6-methanesulfanylpyridin-3-yl)-N-(5-chlorothiazol-2-yl)acrylamide (EXAMPLE 6, 120 mg, 0.32 mmol) in THF-MeOH (1:1, 6 mL) at 0° C. After 15 min, saturated aqueous NaHCO₃ (5 mL) and 10% aqueous Na₂S₂O₃ (5 mL) were added, then the mixture was extracted with EtOAc (2×10 mL). The combined organic layers were washed with H₂O (10 mL) and brine (10 mL), dried (Na₂SO₄), filtered, and concentrated in vacuo. Chromatographic purification (EtOAc-n-C₆H₁₄, 2:1) of the residue gave the title compound: δ$_H$ (CDCl₃): 1.40-1.62 (m, 4H), 1.70-1.82 (m, 4H), 2.27-2.42 (m, 1H), 2.96 (s, 3H), 7.19 (d, 1H), 7.24 (s, 1H), 7.86 (dd, 1H), 8.14 (d, 1H), 8.52 (dd, 1H), 8.72 (br s, 1H); m/z (APCI+)=396, 398 [M+H]+.

EXAMPLE 65

3-Cyclopentyl-2-(6-methanesulfonylpyridin-3-yl)-N-thiazol-2-ylpropionamide

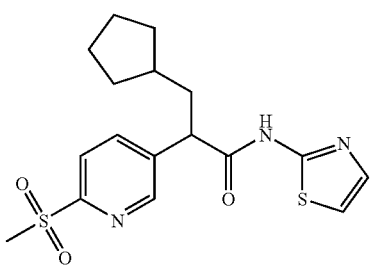

A mixture of (E)-3-cyclopentyl-2-(6-methanesulfonylpyridin-3-yl)-N-thiazol-2-ylacrylamide (EXAMPLE 35, 500 mg, 1.3 mmol), ammonium formate (500 mg, 7.9 mmol), and 10% palladium on charcoal (50% $H_2O$, 500 mg) in MeOH (20 mL) was stirred at 80° C. for 20 h. The solvent was removed in vacuo, then the residue was diluted with EtOAc and filtered through Celite. The filtrate was concentrated and once again diluted with EtOAc, filtered through Celite and concentrated. Purification of the crude product by column chromatography (EtOAc-n-$C_6H_{14}$, 3:7 to 1:1) afforded the title compound: $\delta_H$ (CDCl$_3$): 1.05-1.22 (m, 2H), 1.40-1.85 (m, 7H), 1.95 (dt, 1H), 2.29 (dt, 1H), 3.21 (s, 3H), 3.82 (t, 1H), 7.09 (d, 1H), 7.53 (d, 1H), 8.06 (d, 2H), 8.58 (t, 1H); m/z (APCI$^+$)=380 [M+H]$^+$.

EXAMPLE 66

3-Cyclopentyl-2-(6-mercaptopyridin-3-yl)-N-thiazol-2-ylpropionamide

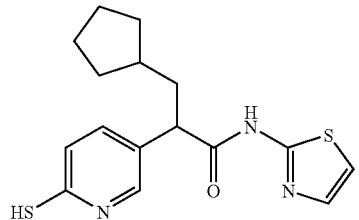

A solution of 3-cyclopentyl-2-(6-fluoropyridin-3-yl)-N-thiazol-2-ylpropionamide (EXAMPLE 14, 350 mg, 1.1 mmol) and NaSMe (1.53 g, 22.0 mmol) in anhydrous, degassed DMSO (4 mL) was stirred at 160° C. (bath) for 1 h. On cooling, the mixture was partitioned between EtOAc (50 mL) and 1M HCl (50 mL). The organic layer was washed with $H_2O$ (20 mL) and brine (50 mL). The solvent was evaporated and the residue recrystallised (EtOAc-1H) to give the title compound: RT$^A$=3.24 min; m/z (ES$^+$)=334.2 [M+H]$^+$.

EXAMPLE 67

3-Cyclopentyl-2-(6-methanesulfinylpyridin-3-yl)-N-thiazol-2-ylpropionamide

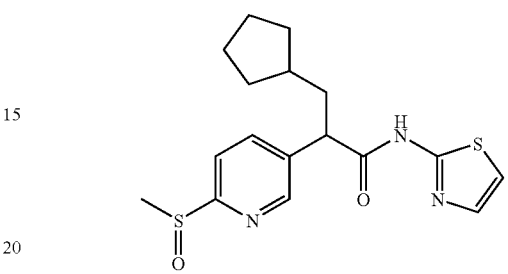

Step 1: MeI (44 µL of a 2.3M solution in anhydrous DMF, 102 µmol) and $K_2CO_3$ (14 mg, 102 µmol) were added to a stirred solution of 3-cyclopentyl-2-(6-mercaptopyridin-3-yl)-N-thiazol-2-ylpropionamide (EXAMPLE 66, 34 mg, 102 µmol) in anhydrous DMF (1 mL). After 16 h, the solvents were evaporated off under reduced pressure, then the residue was partitioned between EtOAc (12 mL) and $H_2O$ (5 mL). The organic layer was washed with $H_2O$ (5 mL) and brine (5 mL), before being dried (MgSO$_4$). The solution was filtered, passed through a short SiO$_2$ plug, and evaporated to give 3-cyclopentyl-2-(6-methylsulfanylpyridin-3-yl)-N-thiazol-2-ylpropionamide: m/z (ES$^+$)=348.2 [M+H]$^+$. Step 2: Oxidation of this thioether (52 mg, 150 µmol), by the protocol described in EXAMPLE 55, gave the title compound: RT$^A$=3.17 min; m/z (ES$^+$)=364.2 [M+H]$^+$.

The compounds listed in TABLE 12 were prepared employing the protocols described in EXAMPLE 67.

TABLE 12

| Ex | Structure | Name | RT$^A$ (min) | m/z (ES$^+$) |
|---|---|---|---|---|
| 68 | 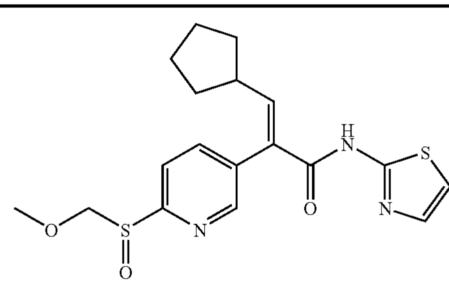 | 3-Cyclopentyl-2-(6-methoxymethanesulfinylpyridin-3-yl)-N-thiazol-2-ylpropionamide | 3.29 | 394.2 [M + H]$^+$ |
| 69 | 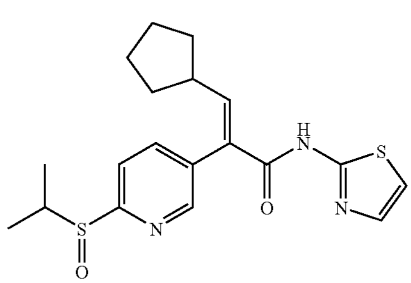 | 3-Cyclopentyl-2-[6-(propane-2-sulfinyl)pyridin-3-yl]-N-thiazol-2-ylpropionamide | 3.47 | 392.2 [M + H]$^+$ |

EXAMPLE 70

3-{5-[2-Cyclopentyl-1-(thiazol-2-ylcarbamoyl)ethyl]pyridin-2-ylsulfanyl}propionic Acid

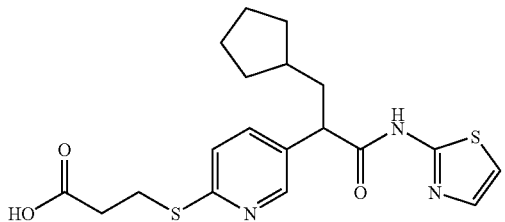

3-Cyclopentyl-2-(6-mercaptopyridin-3-yl)-N-thiazol-2-ylpropionamide (EXAMPLE 66, 100 mg, 300 μmol) was reacted with 3-iodopropionic acid (60 mg, 300 mol), employing the procedure described in Step 1 of EXAMPLE 67, to furnish the title compound: $RT^A$=3.61 min; m/z (ES$^+$)=406.4 [M+H]$^+$.

EXAMPLE 71

3-{5-[2-Cyclopentyl-1-(thiazol-2-ylcarbamoyl)ethyl]pyridine-2-sulfonyl}propionic Acid

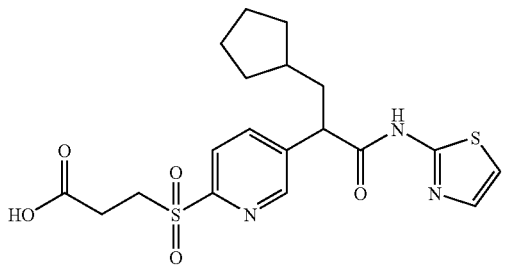

3-{5-[2-Cyclopentyl-1-(thiazol-2-ylcarbamoyl)ethyl]pyridin-2-ylsulfanyl}propionic acid (EXAMPLE 70, 49 mg, 121 mol) was oxidised, employing the protocol described in EXAMPLE 35, to afford the title compound: $RT^A$=3.37 min; m/z (ES$^+$)=438.2 [M+H]$^+$.

EXAMPLE 72

{5-[2-Cyclopentyl-1-(thiazol-2-ylcarbamoyl)ethyl]pyridin-2-ylsulfanyl} acetic Acid

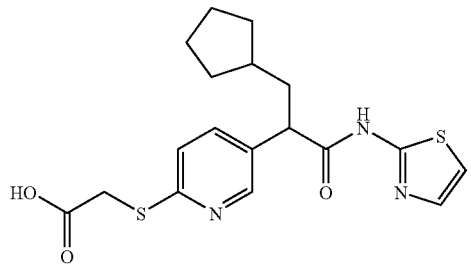

3-Cyclopentyl-2-(6-mercaptopyridin-3-yl)-N-thiazol-2-ylpropionamide (EXAMPLE 66, 50 mg, 150 μmol) was added to a stirred suspension of NaH (12 mg of a 60% dispersion in mineral oil, 300 μmol) in anhydrous DMF (0.8 mL). After 5 min, a solution of chloroacetic acid (14 mg, 150 μmol) in anhydrous DMF (0.4 mL) was added. The reaction was stirred for 15 min, then more NaH (10 mg of a 60% dispersion in mineral oil, 250 μmol) and chloroacetic acid (14 mg, 150 μmol) were added. After 15 min, the reaction mixture was partitioned between EtOAc (10 mL) and saturated aqueous Na$_2$CO$_3$—H$_2$O (1:1, 15 mL). The aqueous phase was acidified to pH 2.5 with 2M HCl, then the resulting precipitate was extracted into EtOAc (15 mL). The EtOAc solution was washed with brine (5 mL), dried (MgSO$_4$), filtered, concentrated, and recrystallised (CH$_2$Cl$_2$—IH) to give the title compound: $RT^A$=3.52 min; m/z (ES$^+$)=392.2 [M+H]$^+$.

EXAMPLE 73

{5-[2-Cyclopentyl-1-(thiazol-2-ylcarbamoyl)ethyl]pyridine-2-sulfonyl}acetic Acid

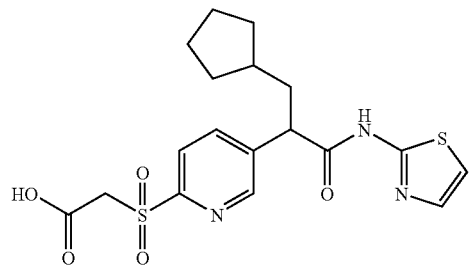

Step 1: 3-Cyclopentyl-2-(6-mercaptopyridin-3-yl)-N-thiazol-2-ylpropionamide (EXAMPLE 66, 94 mg, 283 μmol) was alkylated with tert-butyl bromoacetate (55 mg, 283 μmol), using the procedure described in EXAMPLE 72, to give tert-butyl {5-[2-cyclopentyl-1-(thiazol-2-ylcarbamoyl)ethyl]pyridin-2-ylsulfanyl}acetate: m/z (ES$^+$)=448.3 [M+H]$^+$. Step 2: Oxidation of this thioether, employing the protocol described in EXAMPLE 35, provided tert-butyl {5-[2-cyclopentyl-1-(thiazol-2-ylcarbamoyl)-ethyl]pyridine-2-sulfonyl}acetate: $\delta_H$ (CDCl$_3$): 1.05-1.20 (m, 2H), 1.25 (s, 9H), 1.45-1.85 (m, 7H), 1.90-2.00 (m, 1H), 2.30-2.40 (m, 1H), 3.90-4.00 (m, 1H), 4.30-4.45 (m, 2H), 7.10 (d, 1H), 7.55 (d, 1H), 8.05 (d, 1H), 8.10 (dd, 1H), 8.70 (d, 1H). Step 3: A solution of this compound (48 mg, 100 μmol) in CH$_2$Cl$_2$-TFA (1:3, 4 mL) was stirred at 20° C. for 2 h. Ths solvents were evaporated, then the remainder was treated with saturated aqueous NaHCO$_3$ (5 mL). The resulting solution was acidified with 2M HCl to pH 2, then the mixture was extracted with EtOAc (10 mL+5 mL). The organic layer was concentrated and chromatographed (MeOH—CH$_2$Cl$_2$-AcOH, 2:18:1) to furnish the title compound: $RT^A$=3.37 min; m/z (ES$^+$)=424.1 [M+H]$^+$.

EXAMPLE 74

{5-[2-Cyclopentyl-1-(thiazol-2-ylcarbamoyl)ethyl]pyridine-2-sulfinyl}acetic Acid

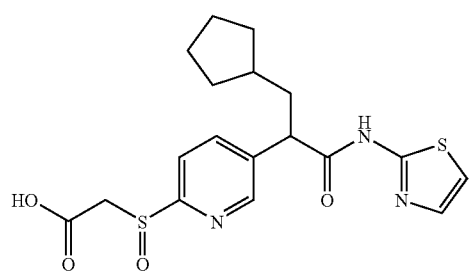

Oxidation of tert-butyl {5-[2-cyclopentyl-1-(thiazol-2-yl-carbamoyl)ethyl]pyridin-2-ylsulfanyl} acetate (see EXAMPLE 73, 61 mg, 136 μmol), by the method described in EXAMPLE 55, gave tert-butyl {5-[2-cyclopentyl-1-(thiazol-2-ylcarbamoyl)ethyl]pyridine-2-sulfinyl}acetate: $\delta_H$ (CDCl$_3$): 1.10-1.25 (m, 2H), 1.35 (s, 4.5H), 1.40 (s, 4.5H), 1.45-1.85 (m, 7H), 1.90-2.00 (m, 1H), 2.30-2.40 (m, 1H), 3.70-3.80 (m, 1H), 3.90-3.95 (m, 1H), 4.00-4.05 (m, 1H), 7.05 (d, 1H), 7.50 (d, 1H), 8.00-8.15 (m, 2H), 8.60 (m, 1H). Removal of the tert-butyl group, employing the conditions described in Step 3 of EXAMPLE 73, afforded the title compound: RT$^A$=3.15 min; m/z (ES$^+$)=408.1 [M+H]$^+$.

EXAMPLE 75

(E)-2-(6-Aminopyridin-3-yl)-N-(5-chlorothiazol-2-yl)-3-cyclopentylacrylamide

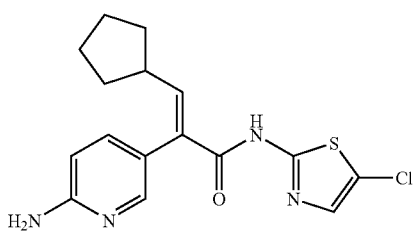

A stirred solution of (E)-tert-butyl {5-[1-(5-chlorothiazol-2-ylcarbamoyl)-2-cyclopentylvinyl]pyridin-2-yl}carbamate (Preparation 18, 212 mg, 473 μmol) in CH$_2$Cl$_2$ (5 mL) was treated with TFA (5 mL, 65.1 mmol). After 2 h, the mixture was evaporated to dryness, then EtOAc (60 mL) was added. The EtOAc solution was washed with H$_2$O-saturated aqueous NaHCO$_3$ (1:1, 20 mL) and brine (20 mL), before being dried (MgSO$_4$). Filtration and solvent evaporation gave a residue that was dissolved in a minimal amount of Et$_2$O. IH was added to the Et$_2$O solution to precipitate a solid, which was collected and dried to furnish the title compound: RT$^A$=3.07 min; m/z (ES$^+$)=349.2 [M+H]$^+$.

The procedure described for EXAMPLE 75 was used to synthesise the compounds listed in TABLE 13.

TABLE 13

| Ex | Structure | Name | RT (min) | m/z (ES$^+$) |
|---|---|---|---|---|
| 76 | 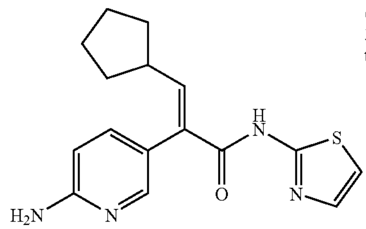 | (E)-2-(6-Aminopyridin-3-yl)-3-cyclopentyl-N-thiazol-2-ylacrylamide | 2.85[A] | 315.1 [M + H]$^+$ |
| 77 | 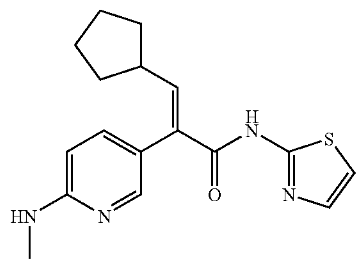 | (E)-3-Cyclopentyl-2-(6-methylaminopyridin-3-yl)-N-thiazol-2-ylacrylamide | 1.04[B] | 329.1 [M + H]$^+$ |

[A] RT measured with Method A.
[B] RT measured with Method B.

EXAMPLE 78

(E)-N-(5-Chlorothiazol-2-yl)-3-cyclopentyl-2-(6-methanesulfonylaminopyridin-3-yl)acrylamide

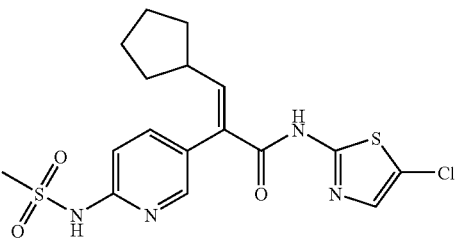

A solution of (E)-2-(6-aminopyridin-3-yl)-N-(5-chlorothiazol-2-yl)-3-cyclopentylacrylamide (EXAMPLE 75, 50 mg, 143 μmol) in anhydrous CH$_2$Cl$_2$ (3 mL) was treated with pyridine (570 μL, 7.1 mmol) and MsCl (170 μL, 2.2 mmol). After stirring for 3 d at 20° C., the reaction mixture was diluted with Et$_2$O (40 mL), before being extracted with 1M NaOH-saturated aqueous NaHCO$_3$ (1:1, 2×15 mL). The combined aqueous extracts were neutralised with 2M HCl, before being extracted with EtOAc (2×50 mL). The combined organic extracts were washed with brine (20 mL), before being dried (MgSO$_4$). Filtration, solvent evaporation, and column chromatography (1:1 IH-EtOAc) furnished the title compound: RT$^A$=3.73 min; m/z (ES$^+$)=427.2 [M+H]$^+$.

The sulfonamides listed in TABLE 14 were prepared from the appropriate aminopyridine using the protocol described in EXAMPLE 78.

TABLE 14

| Ex | Structure | Name | RT^A (min) | m/z (ES+) |
|---|---|---|---|---|
| 79 | 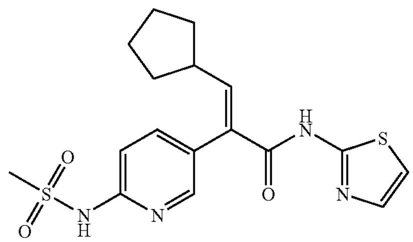 | (E)-3-Cyclopentyl-2-(6-methanesulfonylamino-pyridin-3-yl)-N-thiazol-2-ylacrylamide | 3.45 | 393.2 [M + H]+ |
| 80 | 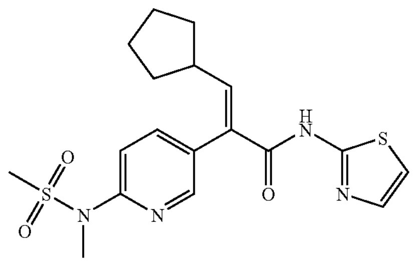 | (E)-3-Cyclopentyl-2-[6-(methanesulfonyl-methylamino)pyridine-3-yl]-N-thiazol-2-ylacrylamide | 3.67 | 407.1 [M + H]+ |

In Vitro GK Activity

Using a protocol similar to that described in WO 00/58293, GK activity was assayed by coupling the production of G6P by GST-GK to the generation of NADPH with G6PDH as the coupling enzyme.

The GK assay was performed at 30° C. in a flat bottom 96-well assay plate from Costar with a final incubation volume of 100 µL. The assay buffer contained: 25 mM Hepes buffer (pH 7.4), 12.5 mM KCl, 5 mM D-Glc, 5 mM ATP, 6.25 mM NADP, 25 mM MgCl$_2$, 1 mM dithiothreitol, test compound or 5% DMSO, 3.0unit/mL G6PDH, and 0.4 µL/mL GST-GK, derived from human liver GK. ATP, G6PDH, and NADP were purchased from Roche Diagnostics. The other reagents were >98% pure and were purchased from Kanto Chemicals. The test compounds were dissolved in DMSO, before being added to the assay buffer without ATP. This mix was preincubated in the temperature controlled chamber of a SPECTRAmax 250 microplate spectrophotometer (Molecular Devices Corporation, Sunnyvale, Calif.) for 10 min, then the reaction was started by the addition of 10 µL ATP solution.

After starting the reaction, the increase in optical density (OD) at 340 nm was monitored over a 10 min incubation period as a measure of GK activity. Sufficient GST-GK was added to produce an increase in OD$_{340}$ over the 10 min incubation period in wells containing 5% DMSO, but no test compound. Preliminary experiments established that the GK reaction was linear over this period of time, even in the presence of activators that produced an 8-fold increase in GK activity. The GK activity in control wells was compared with the activity in wells containing test GK activators. The compound concentrations that produced a 50% increase in GK activity (i.e. FA1.5) were calculated. GK activators achieved FA1.5 at <30 µM.

The above EXAMPLES 1-80 produced EC$_{50}$s ranging from 0.1 to 23.0 µM with max FAs from 1.7 to 6.7.

In Vivo GK Activity

Following an 18 h fasting period, C57BL/6J mice were dosed orally via gavage with GK activator at 50 mg/kg body weight. Blood Glc determinations were made 5 times during the 6 h post-dose study period.

Mice (n=5) were weighed and fasted for 18 h before oral treatment. GK activators were dissolved in the Gelucire vehicle described in WO 00/58293 (EtOH:Gelucire44/14: PEG400 q.s. 4:66:30 v/v/v) at a concentration of 13.3 mg/mL. Mice were dosed orally with 7.5 mL formulation per kg of body weight to equal a 50 mg/kg dose. Immediately prior to dosing, a pre-dose (time zero) blood Glc reading was acquired by snipping off a small portion of the animals' tails (<1 mm) and collecting 15 µL blood for analysis. After GK activator treatment, further blood Glc readings were taken at 1, 2, 4, and 6 h post-dose from the same tail wound. Results were interpreted by comparing the mean blood Glc values of 5 vehicle treated mice with the 5 GK activator treated mice over the 6 h study duration. Compounds were considered active when they exhibited a statistically significant decrease in blood Glc compared to vehicle for 2 consecutive assay time points.

Several of the GK activators exemplified above showed strong GK activator effects in vivo when administered orally following the abovementioned protocol.

What is claimed is:

1. A compound of Formula (I):

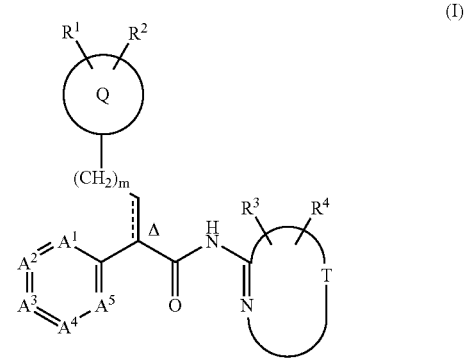

(I)

or a pharmaceutically acceptable salt or N-oxide thereof, wherein:

one of $A^1$, $A^2$, $A^3$, $A^4$ and $A^5$ is N, another of them is C—$R^5$, another of them is C—$R^6$, and the other two are independently either N or CH;

Q is a $C_{3-8}$cycloalkyl;

T together with the —N=C— to which it is attached forms a heteroaryl ring, or a heterocyclic ring where the N=C bond is the only site of unsaturation;

$R^1$ and $R^2$ each independently are hydrogen, halogen, hydroxy, cyano, nitro, vinyl, ethynyl, methoxy, $OCF_nH_{3-n}$, —$N(C_{0-4}alkyl)(C_{0-4}alkyl)$, CHO, or $C_{1-2}$alkyl optionally substituted with 1-5 independent halogen, hydroxy, cyano, methoxy, —$N(C_{0-2}alkyl)(C_{0-2}alkyl)$, $SOCH_3$, or $SO_2CH_3$ substituents; or $R^1$ and $R^2$ together form a carbocyclic ring; or $R^1$ and $R^2$ may be taken together to represent an oxygen atom attached to the ring via a double bond;

$R^3$ and $R^4$ each independently are hydrogen, halogen, $OCF_nH_{3-n}$, methoxy, $CO_2R^{77}$, cyano, nitro, CHO, $CONR^{99}R^{100}$, $CON(OCH_3)CH_3$, or $C_{1-2}$alkyl, or $C_{3-7}$cycloalkyl optionally substituted with 1-5 independent halogen, hydroxy, cyano, methoxy, —$NHCO_2CH_3$, or —$N(C_{0-2}alkyl)(C_{0-2}alkyl)$ substituents; or $R^3$ and $R^4$ together form a 5-8-membered aromatic, or carbocyclic ring;

$R^5$ and $R^6$ each independently are hydrogen, hydroxy, halogen, cyano, nitro, $CO_2R^7$, CHO, $COR^8$, C(OH)$R^7R^8$, C(=NOR$^7$)$R^8$, $CONR^9R^{10}$, $SR^7$, $SOR^8$, $SO_2R^8$, $SO_2NR^9R^{10}$, $CH_2NR^9R^{10}$, $NR^9R^{10}$, $N(C_{0-4}alkyl)SO_2R^8$, $NHCOR^7$, or $C_{1-4}$alkyl group, $C_{2-4}$alkenyl group, $C_{2-4}$alkynyl group, $C_{1-4}$alkoxy group, or aryl group, wherein any group optionally is substituted with 1-6 independent halogen, cyano, nitro, hydroxy, $C_{1-2}$alkoxy, —$N(C_{0-2}alkyl)(C_{0-2}alkyl)$, $C_{1-2}$alkyl, $CF_nH_{3-n}$, aryl, —$COC_{1-2}alkyl$, —$CON(C_{0-2}alkyl)(C_{0-2}alkyl)$, $SCH_3$, $SOCH_3$, $SO_2CH_3$, or —$SO_2N(C_{0-2}alkyl)(C_{0-2}alkyl)$ substituents; or $R^5$ and $R^6$ together form a 5-8-membered carbocyclic ring;

$R^7$ and $R^{77}$ each independently are hydrogen, or $C_{1-4}$alkyl group, $C_{2-4}$alkenyl group, $C_{2-4}$alkynyl group, $C_{3-7}$cycloalkyl group, or aryl group, wherein any group optionally is substituted with 1-6 independent halogen, cyano, nitro, hydroxy, $C_{1-2}$alkoxy, —$N(C_{0-2}alkyl)(C_{0-2}alkyl)$, $C_{1-2}$alkyl, $C_{3-7}$cycloalkyl, $CF_nH_{3-n}$, aryl, $CO_2H$, —$COC_{1-2}alkyl$, —$CON(C_{0-2}alkyl)(C_{0-2}alkyl)$, $SOCH_3$, $SO_2CH_3$, or —$SO_2N(C_{0-2}alkyl)(C_{0-2}alkyl)$ substituents;

$R^8$ is $C_{1-4}$alkyl group, $C_{2-4}$alkenyl group, $C_{2-4}$alkynyl group, $C_{3-7}$cycloalkyl group, or aryl group, wherein any group optionally is substituted with 1-6 independent halogen, cyano, nitro, hydroxy, $C_{1-2}$alkoxy, —$N(C_{0-2}alkyl)(C_{0-2}alkyl)$, $C_{1-2}$alkyl, $C_{3-7}$cycloalkyl, $CF_nH_{3-n}$, aryl, $CO_2H$, —$COC_{1-2}alkyl$, —$CON(C_{0-2}alkyl)(C_{0-2}alkyl)$, $SOCH_3$, $SO_2CH_3$, or —$SO_2N(C_{0-2}alkyl)(C_{0-2}alkyl)$ substituents;

$R^9$, $R^{10}$, $R^{99}$, and $R^{100}$ each independently are hydrogen, or $C_{1-4}$alkyl group, $C_{3-7}$cycloalkyl group, or aryl group, wherein any group optionally is substituted with 1-6 independent halogen, cyano, nitro, hydroxy, $C_{1-2}$alkoxy, —$N(C_{0-2}alkyl)(C_{0-2}alkyl)$, $C_{1-2}$alkyl, $C_{3-7}$cycloalkyl, $CF_nH_{3-n}$, aryl, —$COC_{1-2}alkyl$, —$CON(C_{0-2}alkyl)(C_{0-2}alkyl)$, $SOCH_3$, $SO_2CH_3$, or —$SO_2N(C_{0-2}alkyl)(C_{0-2}alkyl)$ substituents;

n is 1, 2 or 3;

m is 0 or 1;

the dotted line together with the solid line forms an optional double bond, and Δ indicates that the double bond has the (E)-configuration; and with the proviso that Formula (I) does not represent 3-cyclopentyl-2-pyridin-4-yl-N-thiazol-2-ylpropionamide.

2. A compound according to claim 1, or a pharmaceutically acceptable salt or N-oxide thereof, wherein
the dotted line together with the solid line forms a double bond;
$A^3$ is C—$R^5$, $A^4$ is C—$R^6$, one of $A^1$, $A^2$ and $A^5$ is N, and the other two are CH.

3. A compound according to claim 1, or a pharmaceutically acceptable salt or N-oxide thereof, wherein
the dotted line together with the solid line forms a double bond;
$A^3$ is C—$R^5$, $A^4$ is N, one of $A^1$, $A^2$ and $A^5$ is N, and the other two are CH.

4. A compound according to claim 3, or a pharmaceutically acceptable salt or N-oxide thereof, wherein Q is a $C_{3-8}$cycloalkyl ring.

5. A compound according to claim 1, or a pharmaceutically acceptable salt or N-oxide thereof, wherein
the dotted line together with the solid line forms a single bond;
$A^3$ is C—$R^5$, $A^4$ is C—$R^6$, one of $A^1$, $A^2$ and $A^5$ is N, and the other two are CH.

6. A compound according to claim 1, or a pharmaceutically acceptable salt or N-oxide thereof, wherein Q is cyclopentyl or cyclohexyl.

7. A compound according to claim 1, or a pharmaceutically acceptable salt or N-oxide thereof, wherein the group of formula is 2-pyridyl, 2-pyrazinyl, 2-pyrimidinyl, 4-pyrimidinyl, 3-(1H-pyrazolyl), 2-(1H-imidazolyl) 5-[1,2,4]thiadiazolyl, 2-[1,3,4]thiadiazolyl, 2-(4,5-dihydrothiazolyl), 3-isoxazolyl, 2-oxazolyl, or 2-thiazolyl.

8. A compound according to claim 1, or a pharmaceutically acceptable salt or N-oxide thereof, wherein the dotted line together with the solid line forms a single bond, and the absolute configuration at the asymmetric centre α to the amide carbonyl carbon is (R).

9. A compound according to claim 1 wherein $R^3$ is hydrogen, halogen, $C_{1-2}$alkyl, or trifluoromethyl; and $R^4$ is hydrogen or methyl.

10. A compound selected from:
2-(6-Chloropyridin-3-yl)-3-cyclopentyl-N-thiazol-2-yl-propionamide;
3-Cyclopentyl-2-(6-phenylpyridin-3-yl)-N-thiazol-2-yl-propionamide;
3-Cyclopentyl-2-pyridin-3-yl-N-thiazol-2-ylpropionamide;
(E)-3-Cyclopentyl-2-(6-methylsulfanylpyridin-3-yl)-N-thiazol-2-ylacrylamide;
(E)-N-(5-Chlorothiazol-2-yl)-3-cyclopentyl-2-(6-methylsulfanylpyridin-3-yl)acrylamide;
(E)-3-Cyclopentyl-2-(6-ethylsulfanylpyridin-3-yl)-N-thiazol-2-ylacrylamide;
(E)-N-(5-Chlorothiazol-2-yl)-3-cyclopentyl-2-(6-ethylsulfanylpyridin-3-yl)acrylamide;
(E)-3-Cyclopentyl-2-(5-methylsulfanylpyridin-2-yl)-N-thiazol-2-ylacrylamide;
(E)-N-(5-Chlorothiazol-2-yl)-3-cyclopentyl-2-(5-methylsulfanylpyridin-2-yl)acrylamide;
3-Cyclopentyl-2-(6-fluoropyridin-3-yl)-N-thiazol-2-yl-propionamide;
(E)-3-Cyclopentyl-2-(2-propylsulfanylpyrimidin-5-yl)-N-thiazol-2-ylacrylamide;
N-(5-Chloropyridin-2-yl)-3-cyclopentyl-2-(6-cyclopropanesulfonylpyridin-3-yl)propionamide;

3-Cyclopentyl-2-(6-cyclopropanesulfonylpyridin-3-yl)-N-[1,2,4]thiadiazol-5-ylpropionamide;
3-Cyclopentyl-2-(6-cyclopropanesulfonylpyridin-3-yl)-N-[1,3,4]thiadiazol-2-ylpropionamide;
3-Cyclopentyl-2-(6-cyclopropanesulfonylpyridin-3-yl)-N-pyrimidin-2-ylpropionamide;
3-Cyclopentyl-2-(6-cyclopropanesulfonylpyridin-3-yl)-N-(4-methyloxazol-2-yl)propionamide;
3-Cyclopentyl-2-(6-cyclopropanesulfonylpyridin-3-yl)-N-(4-methylpyridin-2-yl)propionamide;
3-Cyclopentyl-2-(6-cyclopropanesulfonylpyridin-3-yl)-N-(6-methylpyridin-2-yl)propionamide;
3-Cyclopentyl-2-(6-cyclopropanesulfonylpyridin-3-yl)-N-isoxazol-3-ylpropionamide;
3-Cyclopentyl-2-(6-cyclopropanesulfonylpyridin-3-yl)-N-(5-fluoropyridin-2-yl)propionamide;
3-Cyclopentyl-2-(6-cyclopropanesulfonylpyridin-3-yl)-N-(1-methyl-1H-pyrazol-3-yl)propionamide;
3-Cyclopentyl-2-(6-cyclopropanesulfonylpyridin-3-yl)-N-(5-methylpyridin-2-yl)propionamide;
3-Cyclopentyl-2-(6-cyclopropanesulfonylpyridin-3-yl)-N-pyridin-2-ylpropionamide;
N-Benzothiazol-2-yl-3-cyclopentyl-2-(6-cyclopropanesulfonylpyridin-3-yl)propionamide;
3-Cyclopentyl-2-(6-cyclopropanesulfonylpyridin-3-yl)-N-pyrazin-2-ylpropionamide;
N-(6-Chloropyrazin-2-yl)-3-cyclopentyl-2-(6-cyclopropanesulfonylpyridin-3-yl)propionamide;
3-Cyclopentyl-2-(6-cyclopropanesulfonylpyridin-3-yl)-N-pyrimidin-4-ylpropionamide;
3-Cyclopentyl-2-(6-cyclopropanesulfonylpyridin-3-yl)-N-(3-methyl-[1,2,4]thiadiazol-5-yl)propionamide;
(E)-3-Cyclopentyl-2-(6-methanesulfonylpyridin-3-yl)-N-thiazol-2-ylacrylamide;
(E)-N-(5-Chlorothiazol-2-yl)-3-cyclopentyl-2-(6-methanesulfonylpyridin-3-yl)acrylamide;
(E)-3-Cyclopentyl-2-(6-ethanesulfonylpyridin-3-yl)-N-thiazol-2-ylacrylamide;
(E)-N-(5-Chlorothiazol-2-yl)-3-cyclopentyl-2-(6-ethanesulfonylpyridin-3-yl)acrylamide;
(E)-3-Cyclopentyl-2-(5-methanesulfonylpyridin-2-yl)-N-thiazol-2-ylacrylamide;
(E)-N-(5-Bromothiazol-2-yl)-3-cyclopentyl-2-(6-methanesulfonylpyridin-3-yl)acrylamide;
(E)-3-Cyclopentyl-2-(6-cyclopropanesulfonylpyridin-3-yl)-N-thiazol-2-ylacrylamide;
(E)-N-(5-Chlorothiazol-2-yl)-3-cyclopentyl-2-(6-cyclopropanesulfonylpyridin-3-yl)acrylamide;
(E)-3-Cyclopentyl-2-(6-cyclopropanesulfonylpyridin-3-yl)-N-(5-fluorothiazol-2-yl)acrylamide;
(E)-2-[3-Cyclopentyl-2-(6-cyclopropanesulfonylpyridin-3-yl)acryloylamino]thiazole-5-carboxylic acid methylamide;
(E)-N-(5-Chlorothiazol-2-yl)-3-cyclopentyl-2-(5-methanesulfonylpyridin-2-yl)acrylamide;
(E)-N-(5-Chlorothiazol-2-yl)-3-cyclopentyl-2-(5-methanesulfinylpyridin-2-yl)acrylamide;
(E)-2-[5-Chloro-6-(propane-1-sulfonyl)pyridin-3-yl]-3-cyclopentyl-N-thiazol-2-ylacrylamide;
(E)-2-[5-Chloro-6-(propane-1-sulfinyl)pyridin-3-yl]-3-cyclopentyl-N-thiazol-2-ylacrylamide;
(E)-2-(5-Chloro-6-methanesulfonylpyridin-3-yl)-3-cyclopentyl-N-thiazol-2-ylacrylamide;
(E)-2-(5-Chloro-6-methanesulfinylpyridin-3-yl)-3-cyclopentyl-N-thiazol-2-ylacrylamide;
(E)-2-(5-Chloro-6-methanesulfonylpyridin-3-yl)-N-(5-chlorothiazol-2-yl)-3-cyclopentylacrylamide;
(E)-2-(5-Chloro-6-methanesulfinylpyridin-3-yl)-N-(5-chlorothiazol-2-yl)-3-cyclopentylacrylamide;
(E)-3-Cyclopentyl-N-(5-fluorothiazol-2-yl)-2-(6-methanesulfonylpyridin-3-yl)acrylamide;
(E)-3-Cyclopentyl-N-(5-fluorothiazol-2-yl)-2-(6-methanesulfinylpyridin-3-yl)acrylamide;
(E)-3-Cyclopentyl-2-(6-methanesulfinylpyridin-3-yl)-N-thiazol-2-ylacrylamide;
(E)-3-Cyclopentyl-2-(6-ethanesulfinylpyridin-3-yl)-N-thiazol-2-ylacrylamide;
(E)-N-(5-Chlorothiazol-2-yl)-3-cyclopentyl-2-(6-ethanesulfinylpyridin-3-yl)acrylamide;
(E)-3-Cyclopentyl-2-(5-methanesulfinylpyridin-2-yl)-N-thiazol-2-ylacrylamide;
(E)-3-Cyclopentyl-2-[2-(propane-1-sulfinyl)pyrimidin-5-yl]-N-thiazol-2-ylacrylamide;
(E)-3-Cyclopentyl-2-(6-ethanesulfinylpyridin-3-yl)-N-(5-fluorothiazol-2-yl)acrylamide;
(E)-3-Cyclopentyl-2-(6-cyclopropanesulfinylpyridin-3-yl)-N-thiazol-2-ylacrylamide;
(E)-N-(5-Chlorothiazol-2-yl)-3-cyclopentyl-2-(6-cyclopropanesulfinylpyridin-3-yl)acrylamide;
(E)-3-Cyclopentyl-2-(6-cyclopropanesulfinylpyridin-3-yl)-N-(5-fluorothiazol-2-yl)acrylamide;
(E)-3-Cyclopentyl-2-(6-methanesulfinylpyridin-3-yl)-N-(5-chlorothiazol-2-yl)acrylamide;
3-Cyclopentyl-2-(6-methanesulfonylpyridin-3-yl)-N-thiazol-2-ylpropionamide;
3-Cyclopentyl-2-(6-mercaptopyridin-3-yl)-N-thiazol-2-ylpropionamide;
3-Cyclopentyl-2-(6-methanesulfinylpyridin-3-yl)-N-thiazol-2-ylpropionamide;
3-Cyclopentyl-2-(6-methoxymethanesulfinylpyridin-3-yl)-N-thiazol-2-ylpropionamide;
3-Cyclopentyl-2-[6-(propane-2-sulfinyl)pyridin-3-yl]-N-thiazol-2-ylpropionamide;
3-{5-[2-Cyclopentyl-1-(thiazol-2-ylcarbamoyl)ethyl]pyridin-2-ylsulfanyl}propionic acid;
3-{5-[2-Cyclopentyl-1-(thiazol-2-ylcarbamoyl)ethyl]pyridine-2-sulfonyl}propionic acid;
{5-[2-Cyclopentyl-1-(thiazol-2-ylcarbamoyl)ethyl]pyridin-2-ylsulfanyl}acetic acid;
{5-[2-Cyclopentyl-1-(thiazol-2-ylcarbamoyl)ethyl]pyridine-2-sulfonyl}acetic acid;
{5-[2-Cyclopentyl-1-(thiazol-2-ylcarbamoyl)ethyl]pyridine-2-sulfinyl}acetic acid;
(E)-2-(6-Aminopyridin-3-yl)-N-(5-chlorothiazol-2-yl)-3-cyclopentylacrylamide;
(E)-2-(6-Aminopyridin-3-yl)-3-cyclopentyl-N-thiazol-2-ylacrylamide;
(E)-3-Cyclopentyl-2-(6-methylaminopyridin-3-yl)-N-thiazol-2-ylacrylamide;
(E)-N-(5-Chlorothiazol-2-yl)-3-cyclopentyl-2-(6-methanesulfonylaminopyridin-3-yl)acrylamide;
(E)-3-Cyclopentyl-2-(6-methanesulfonylaminopyridin-3-yl)-N-thiazol-2-ylacrylamide;
(E)-3-Cyclopentyl-2-[6-(methanesulfonylmethylamino)pyridin-3-yl]-N-thiazol-2-ylacrylamide;
or a pharmaceutically acceptable salt or N-oxide thereof.

11. A pharmaceutical composition comprising a compound according to claim 1, or a pharmaceutically acceptable salt or N-oxide thereof, and a pharmaceutically acceptable carrier.

12. A method treatment of hyperglycemia or diabetes comprising a step of administering an effective amount of the compound according to claim 1, or a pharmaceutically acceptable salt or N-oxide thereof.

13. A method of prevention of diabetes in a human demonstrating pre-diabetic hyperglycemia or impaired glucose tolerance comprising a step of administering an effective prophylactic amount of the compound according to claim 1, or a pharmaceutically acceptable salt or N-oxide thereof.

14. A process for the preparation of a compound of Formula (Ia):

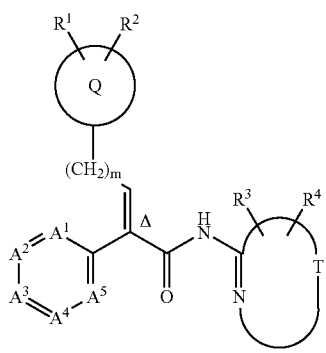

(Ia)

said process comprising a step of the condensation of a compound of Formula (IV):

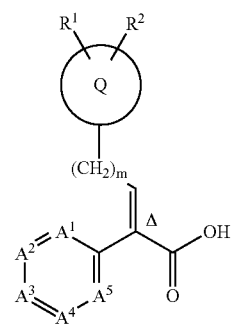

IV with a compound of Formula (V):

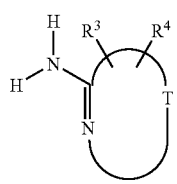

(V)

wherein $A^1$—$A^5$, Q, T, $R^1$—$R^4$, m and Δ are as defined in claim 1.

15. A process for the preparation of a compound of Formula (Ib):

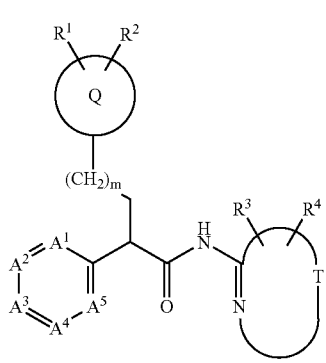

(Ib)

said process comprising a step of the condensation of a compound of Formula (VIII):

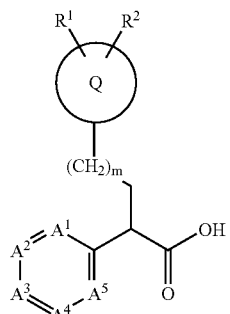

(VIII)

with a compound of Formula (V):

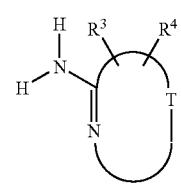

(V)

wherein $A^1$—$A^5$, Q, T, $R^1$—$R^4$ and m are as defined in claim 1.

16. A compound of Formula (IV):

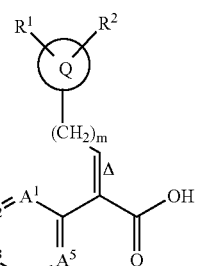

IV wherein $A^1$—$A^5$, Q, $R^1$, $R^2$, m and Δ are as defined in claim 1.

17. A compound of Formula (VIII):

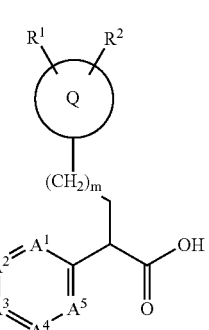

VIII wherein $A^1$—$A^5$, Q, $R^1$, $R^2$ and m are as defined in claim 1.

* * * * *